US011766362B2

(12) United States Patent
Mercer et al.

(10) Patent No.: US 11,766,362 B2
(45) Date of Patent: Sep. 26, 2023

(54) MULTI-LAYER ABDOMINAL CLOSURE DRESSING WITH INSTILLATION CAPABILITIES

(71) Applicant: KCI Licensing, Inc., San Antonio, TX (US)

(72) Inventors: David Richard Mercer, San Antonio, TX (US); James Killingworth Seddon, Ferndown (GB); Braden King-fung Leung, San Antonio, TX (US); Thomas Edwards, Southampton (GB); Colin John Hall, Poole (GB); Benjamin Andrew Pratt, Poole (GB); Tyler H. Simmons, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 356 days.

(21) Appl. No.: 15/877,836

(22) Filed: Jan. 23, 2018

(65) Prior Publication Data

US 2018/0214315 A1    Aug. 2, 2018

Related U.S. Application Data

(60) Provisional application No. 62/451,284, filed on Jan. 27, 2017.

(51) Int. Cl.
*A61F 13/00* (2006.01)
*A61M 39/08* (2006.01)
(Continued)

(52) U.S. Cl.
CPC .. *A61F 13/00068* (2013.01); *A61F 13/00017* (2013.01); *A61F 13/00029* (2013.01);
(Continued)

(58) Field of Classification Search
CPC ..................... A61F 13/00068; A61M 1/0058
See application file for complete search history.

(56) References Cited

U.S. PATENT DOCUMENTS 1,355,846  A    10/1920  Rannells
2,547,758  A     4/1951  Keeling
(Continued)

FOREIGN PATENT DOCUMENTS

AU    550575 B2    3/1986
AU    745271 B2    3/2002
(Continued)

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
(Continued)

*Primary Examiner* — Adam Marcetich
*Assistant Examiner* — Meagan Ngo

(57) ABSTRACT

A treatment system for applying negative pressure therapy and fluid instillation treatment to a tissue site, particularly an abdominal tissue site, is disclosed. In some embodiments, the treatment system may include a dressing member, a plurality of fluid removal pathways, a fluid instillation matrix, a drape, a negative-pressure source, and a fluid instillation source. Instillation fluid may be delivered from the fluid instillation source to the tissue site through the fluid instillation matrix, and negative pressure may be communicated and fluid withdrawn from the tissue site through the plurality of fluid removal pathways.

28 Claims, 24 Drawing Sheets

(51) Int. Cl.
    *A61M 1/00*      (2006.01)
    *A61M 39/24*     (2006.01)
(52) U.S. Cl.
    CPC ......... *A61F 13/00987* (2013.01); *A61M 1/85* (2021.05); *A61M 1/915* (2021.05); *A61M 1/916* (2021.05); *A61M 1/918* (2021.05); *A61M 1/92* (2021.05); *A61M 39/08* (2013.01); *A61F 2013/0017* (2013.01); *A61M 2039/244* (2013.01); *A61M 2210/1021* (2013.01)

(56) References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 7,846,141 | B2 | 12/2010 | Weston |
| 8,062,273 | B2 | 11/2011 | Weston |
| 8,216,198 | B2 | 7/2012 | Heagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2002/0150720 | A1* | 10/2002 | Howard .............. A61M 1/0058 428/131 |
| 2009/0254054 | A1* | 10/2009 | Blott .................. A61M 3/0208 604/290 |
| 2009/0259203 | A1* | 10/2009 | Hu .................... A61F 13/00068 604/290 |
| 2009/0312727 | A1* | 12/2009 | Heaton ................ A61M 1/008 604/318 |
| 2010/0069829 | A1* | 3/2010 | Hutchinson ....... A61F 13/00068 604/28 |
| 2010/0087767 | A1* | 4/2010 | McNeil ................ A61M 27/00 602/42 |
| 2010/0106115 | A1* | 4/2010 | Hardman ........... A61F 13/00025 604/319 |
| 2011/0054283 | A1* | 3/2011 | Shuler ................ A61B 5/14539 600/364 |
| 2011/0224630 | A1* | 9/2011 | Simmons ............ A61M 1/0088 604/317 |
| 2011/0224631 | A1* | 9/2011 | Simmons .......... A61F 13/00995 604/319 |

(56) References Cited

U.S. PATENT DOCUMENTS

| | | | |
|---|---|---|---|
| 2011/0257611 A1* | 10/2011 | Locke | A61M 1/90 604/319 |
| 2013/0165821 A1* | 6/2013 | Freedman | A61M 1/0084 601/2 |
| 2014/0163491 A1 | 6/2014 | Schuessler et al. | |
| 2014/0249495 A1* | 9/2014 | Mumby | A61F 13/0253 604/359 |
| 2015/0080788 A1 | 3/2015 | Blott et al. | |
| 2016/0193394 A1 | 7/2016 | Simmons et al. | |
| 2016/0193395 A1 | 7/2016 | Stevenson et al. | |
| 2016/0199550 A1 | 7/2016 | Seddon et al. | |
| 2017/0028113 A1* | 2/2017 | Shuler | A61F 13/0216 |
| 2017/0209641 A1 | 7/2017 | Mercer et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0117632 A2 | 9/1984 |
| EP | 1 742 684 A1 | 1/2007 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2012162287 A1 | 11/2012 |
| WO | 2016015001 A2 | 1/2016 |

OTHER PUBLICATIONS

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and ceilified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

European Examination and Search Report for Corresponding Application No. 18702888, dated Mar. 1, 2022.

\* cited by examiner

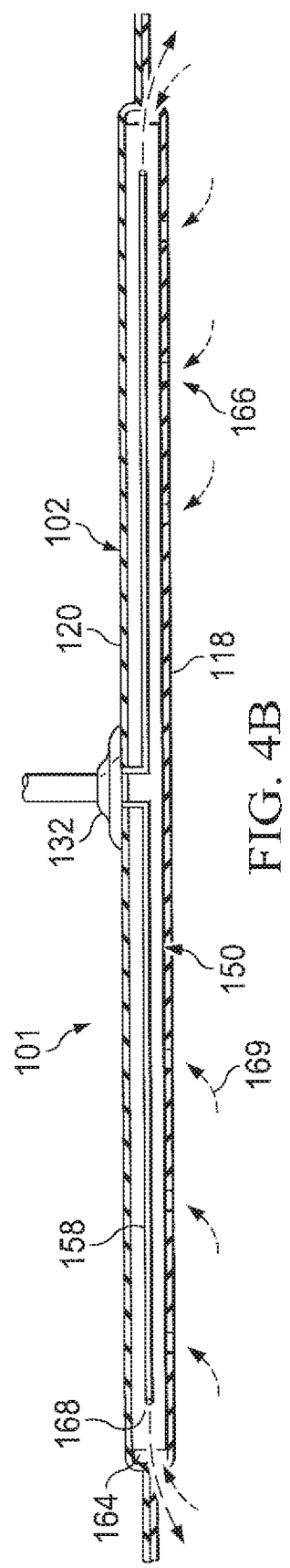

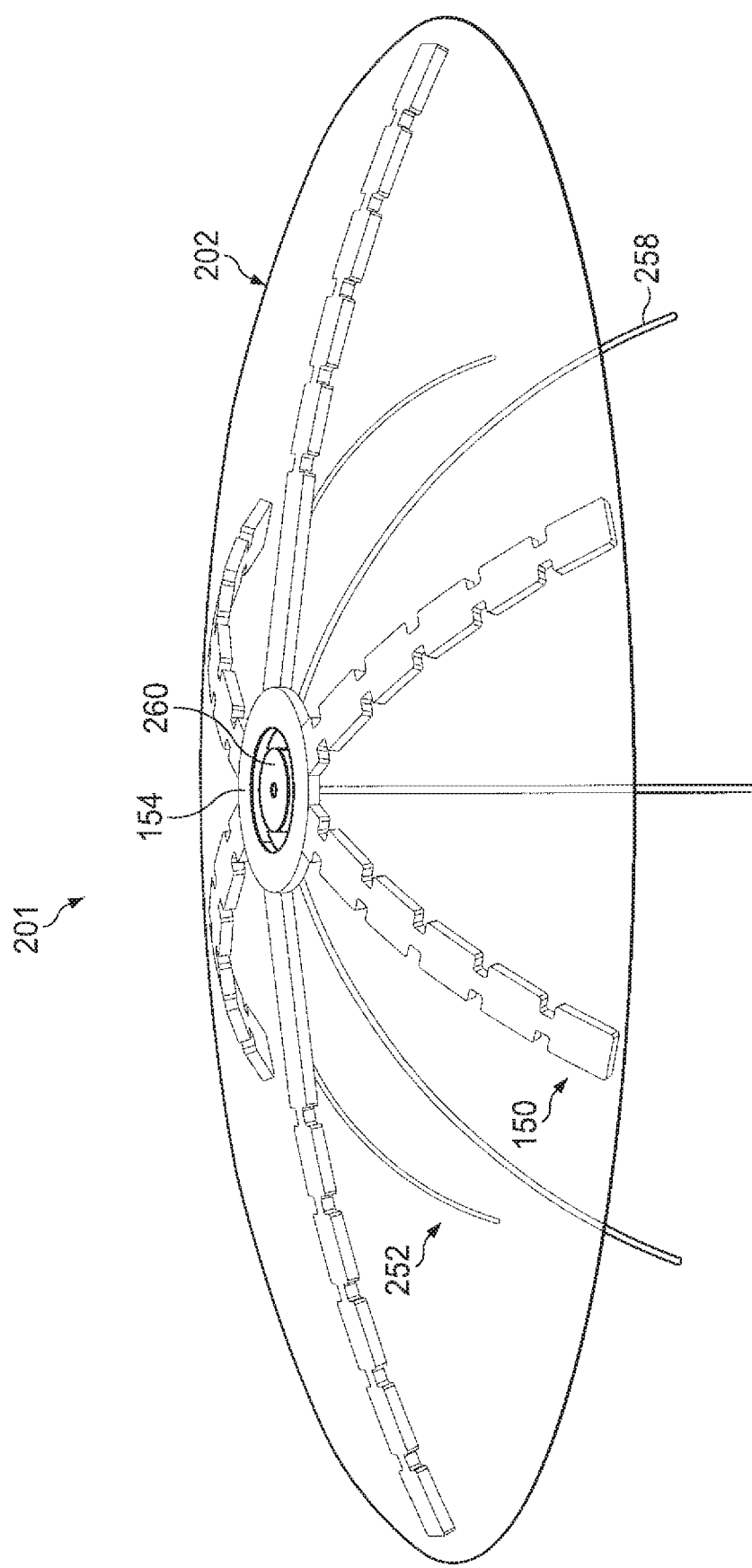

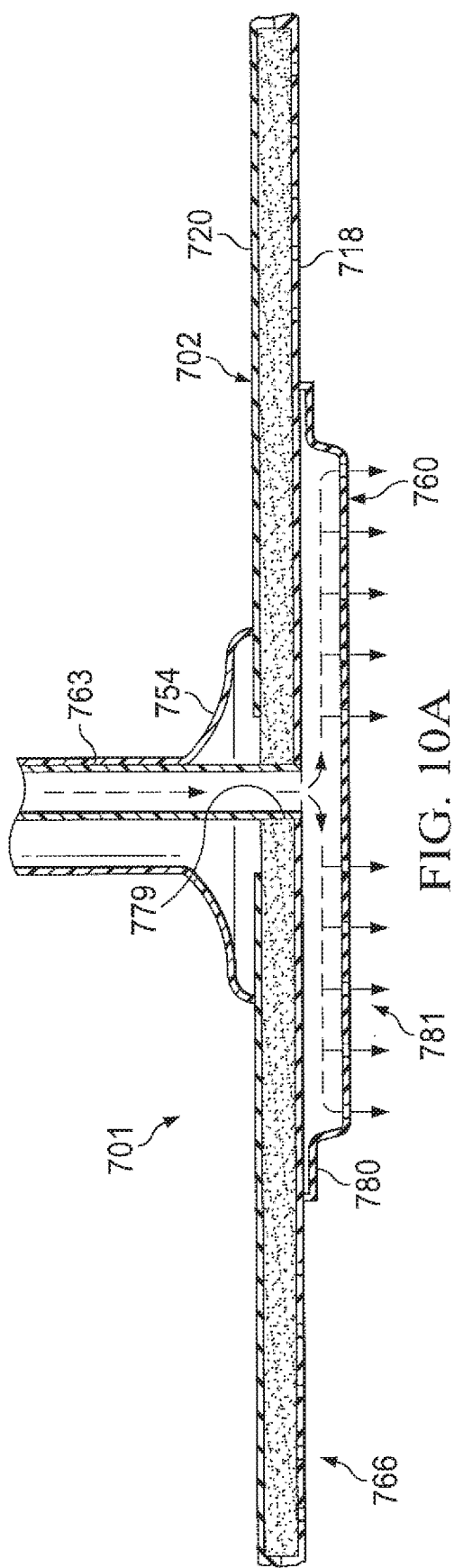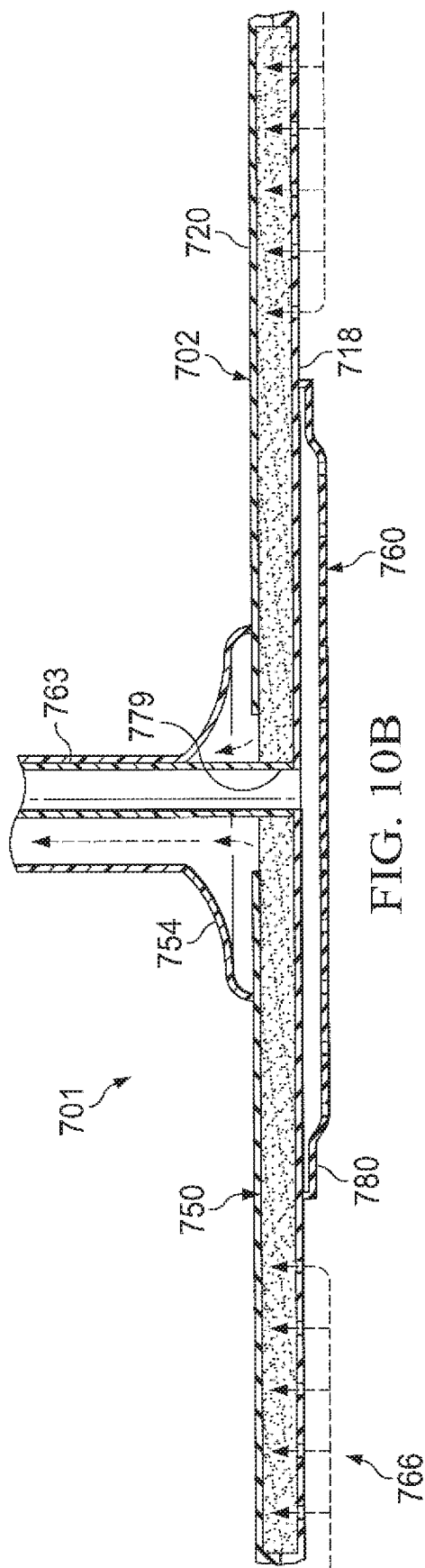

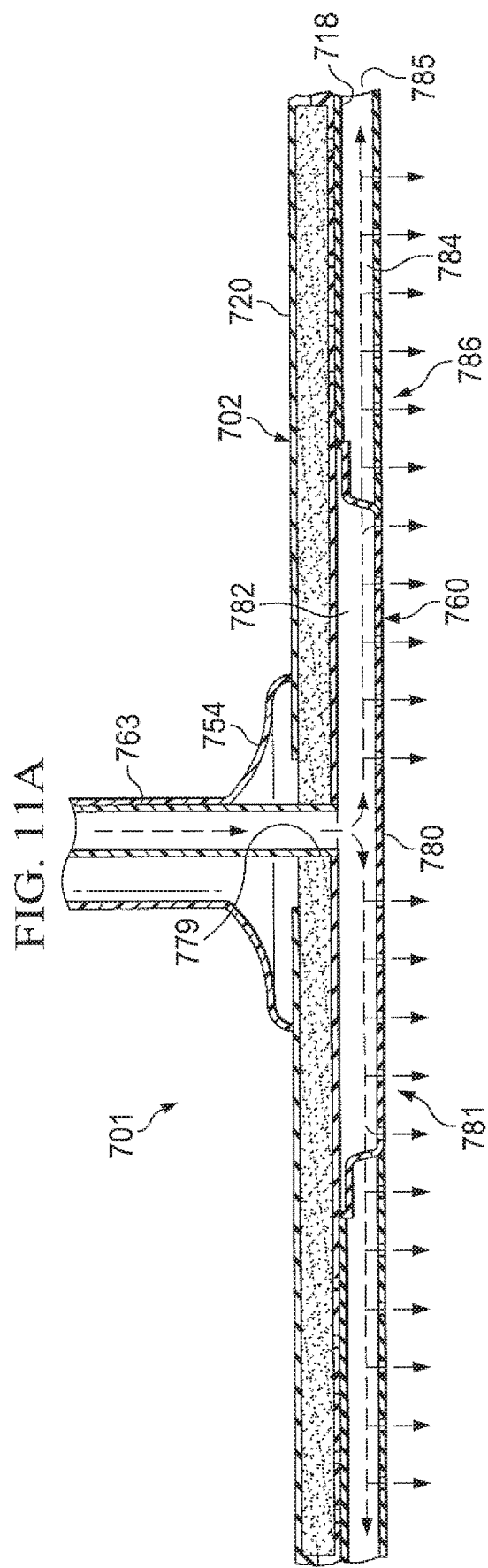

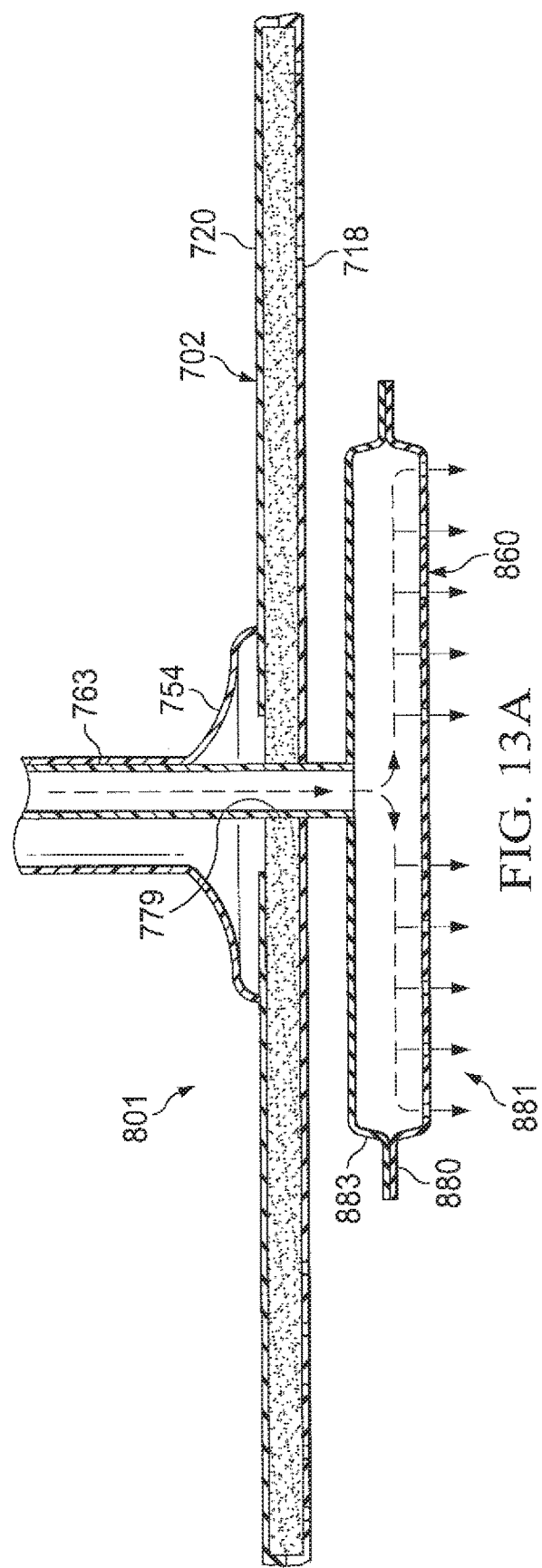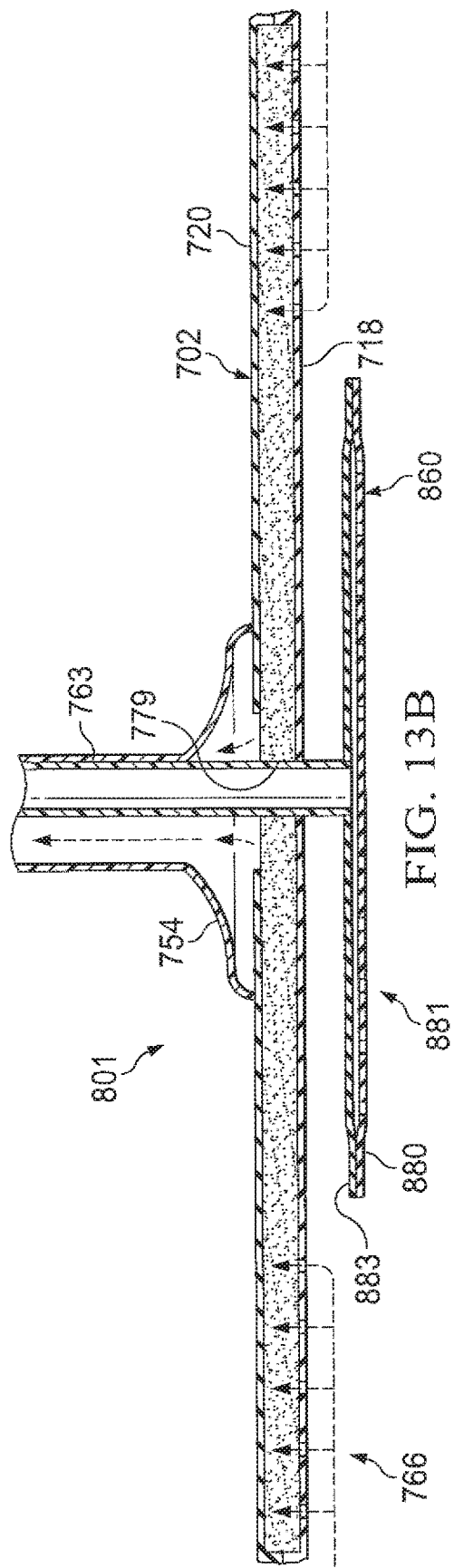

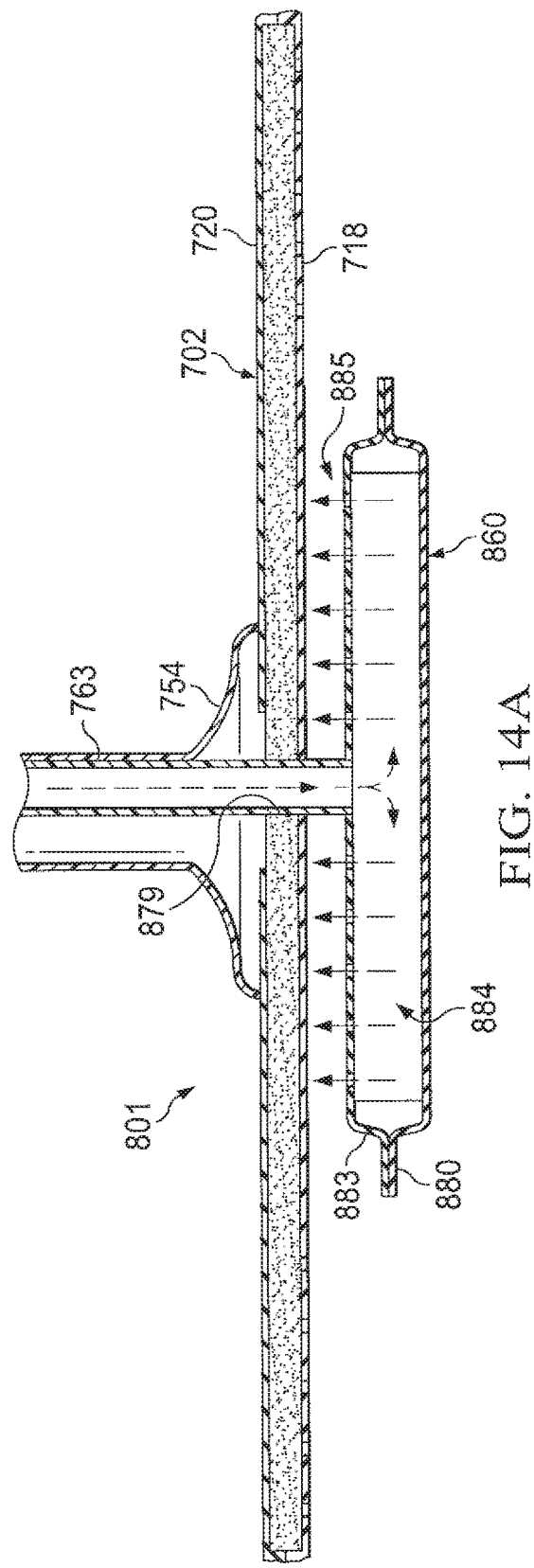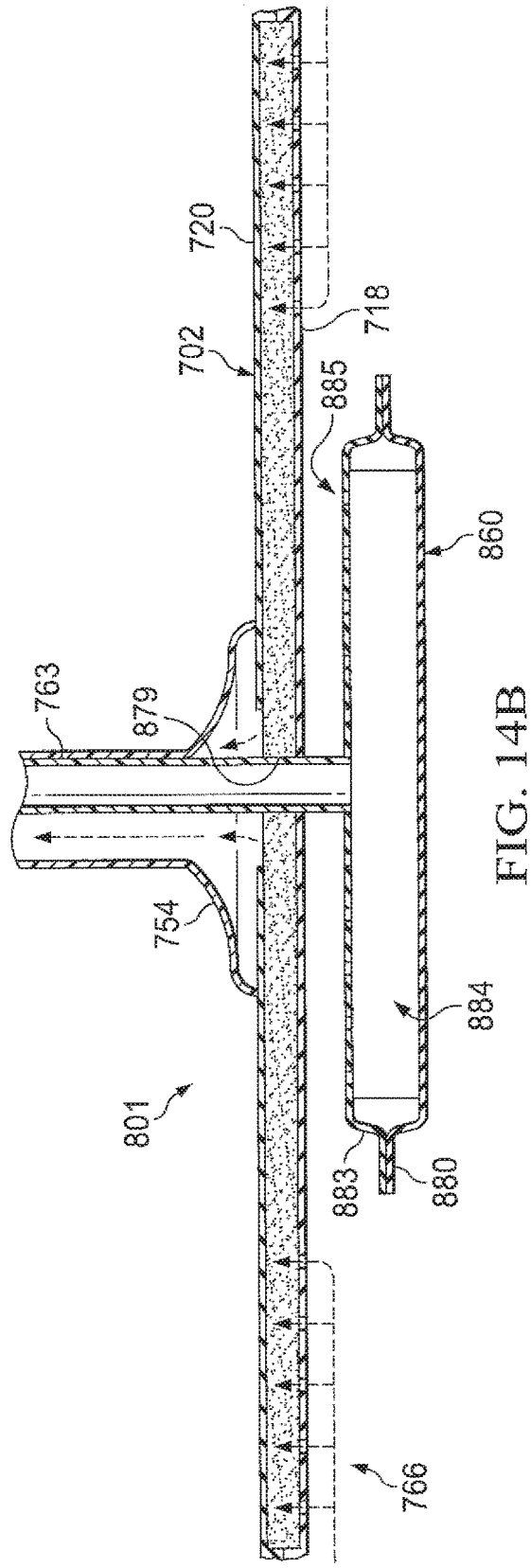

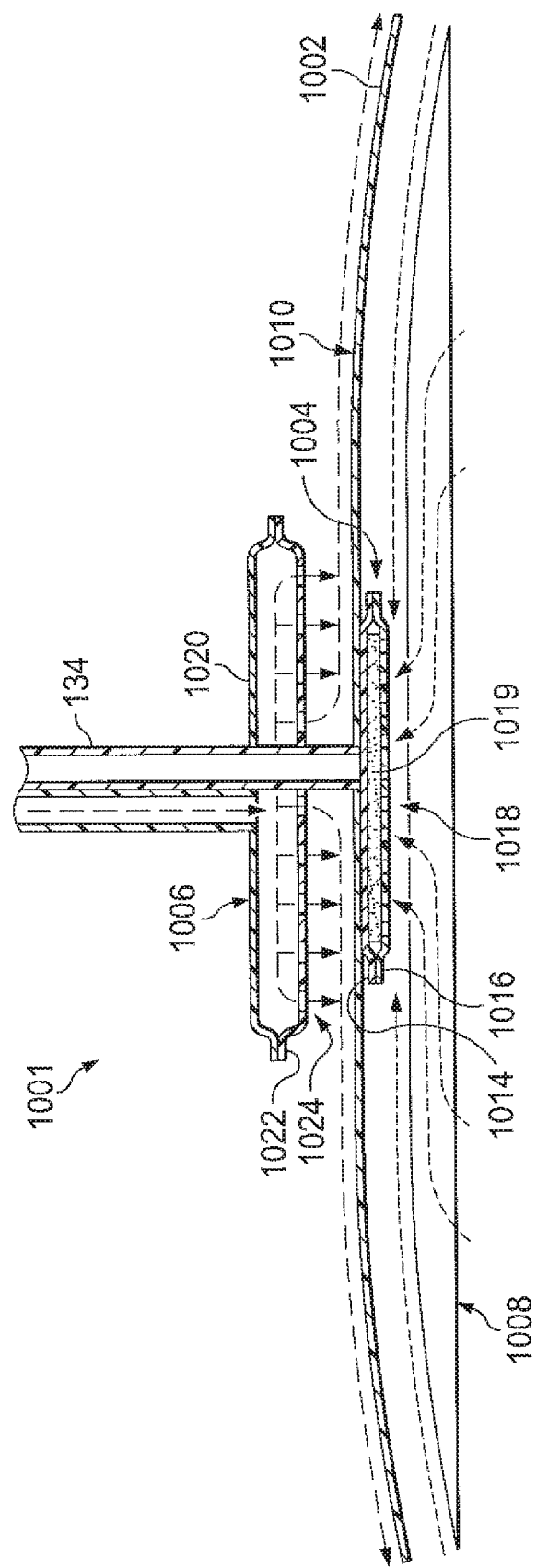

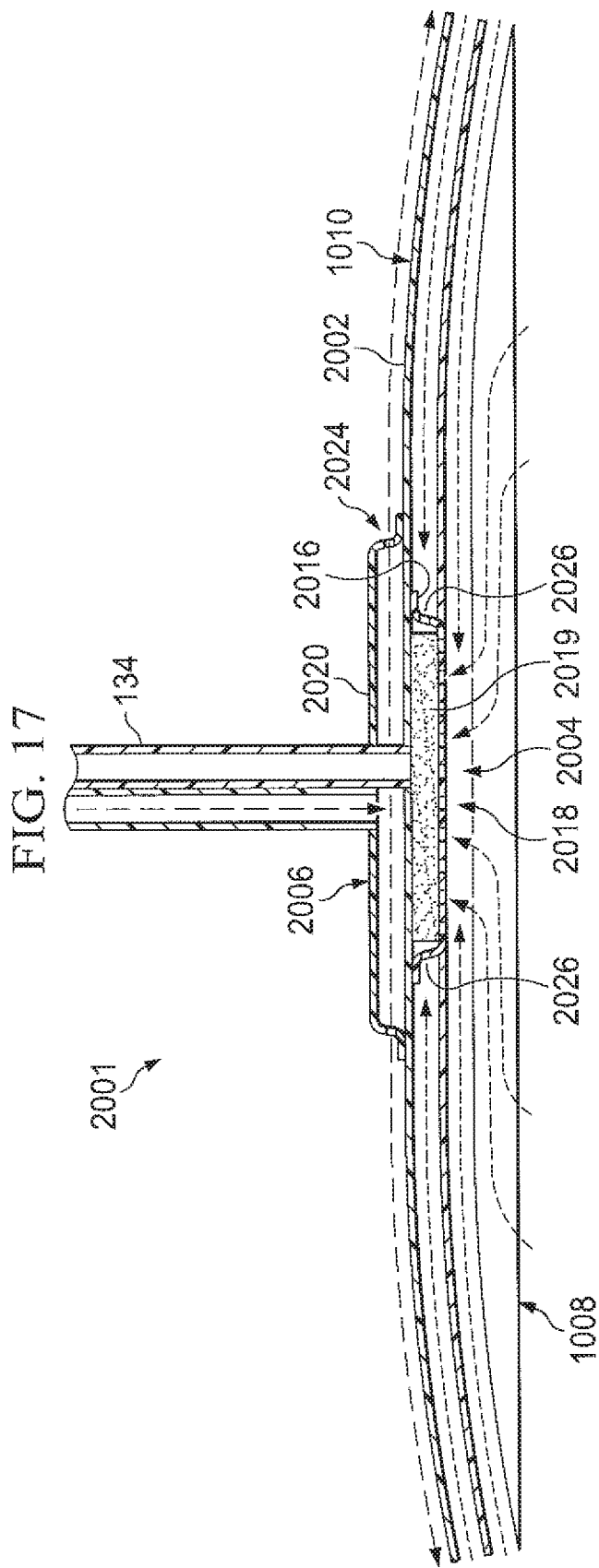

MULTI-LAYER ABDOMINAL CLOSURE DRESSING WITH INSTILLATION CAPABILITIES

CROSS-REFERENCE TO RELATED APPLICATIONS

This application claims the priority benefit of U.S. Provisional Application No. 62/451,284, entitled "Multi-Layer Abdominal Closure Dressing with Instillation Capabilities", filed Jan. 27, 2017, which is incorporated herein by reference in its entirety.

TECHNICAL FIELD

The invention set forth in the appended claims relates generally to tissue treatment systems and more particularly, but without limitation, to abdominal treatment systems with negative pressure and instillation.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

Challenges can exist with distributing fluids to and extracting fluids from a tissue site being subjected to negative-pressure therapy or fluid instillation. For example, tissue sites may vary in volume, size, geometry, orientation, and other factors. Further, access to these tissue sites may be restricted. These and other factors can make extraction of waste fluids from the tissue site and distribution of therapeutic fluids to the tissue site difficult to perform in a uniform or even manner. Further, directional changes in fluid flow between negative-pressure therapy cycles and instillation fluid cycles can force waste fluids being extracted during a negative-pressure therapy cycle back into a tissue site upon switching to a fluid instillation cycle.

Types of tissue sites that may present particular difficulties may include locations such as a peritoneal cavity, and more generally, an abdominal cavity. When a tissue site involves the abdominal cavity, a treatment system that may allow for improved and efficient care, and may address such complications as peritonitis, abdominal compartment syndrome, and infections that might inhibit final healing may be particularly beneficial. Thus, improvements to treatment systems that may adapt to various types of tissue sites and orientations, enhance the uniformity of waste fluid extraction and therapeutic fluid distribution, and increase efficiency and healing times may be desirable.

BRIEF SUMMARY

New and useful systems, apparatuses, and methods for cleansing an abdominal cavity in a negative-pressure therapy environment are set forth in the following summary and description, as well as in the appended claims. Illustrative embodiments are also provided to enable a person skilled in the art to make and use the claimed subject matter.

For example, in some embodiments, a system for treating a tissue site may include a dressing, a negative-pressure source fluidly coupled to the dressing, and a fluid source fluidly coupled to the dressing. The dressing may be configured for deploying in an abdominal cavity.

In other embodiments, a dressing for treating a tissue site may include a dressing member having a first protective layer, a second protective layer, a chamber, a plurality of fluid removal pathways formed within the chamber, and an instillation matrix enclosed in the chamber. In some embodiments, at least a portion of each of the first protective layer and the second protective layer are joined to create the chamber enclosed between the portions of the first protective layer and the second protective layer.

In yet other embodiments, a dressing for treating a tissue site may include a first impermeable layer, a second impermeable layer positioned against and substantially coextensive with the first impermeable layer, a plurality of fluid removal pathways, and a plurality of fluid delivery channels. The plurality of fluid removal pathways and the plurality of fluid delivery channels may be positioned between the first impermeable layer and the second impermeable layer.

According to still other embodiments, a dressing for treating a tissue site may include a plurality of fluid removal pathways and a fluid instillation matrix. The dressing may include a first impermeable layer and a second impermeable layer. The fluid instillation matrix may include a plurality of fluid delivery pathways, and the fluid instillation matrix may be adjacent a first surface of the dressing.

In additional embodiments, a dressing for treating a tissue site may include a plurality of fluid removal pathways, a fluid instillation matrix, a manifold member, and a drape. The dressing may include a first impermeable layer and a second impermeable layer, as well as a space between the first impermeable layer and the second impermeable layer. The plurality of fluid removal pathways may be positioned within the space between the first impermeable layer and the second impermeable layer. The fluid instillation matrix may be associated with the dressing and may include a plurality of fluid delivery pathways. The manifold member may be positioned adjacent a central portion of the dressing in some embodiments. The drape may be adapted to form a fluid seal around the dressing and the manifold member.

In some further embodiments, a tissue treatment system may include a treatment device configured for deploying in an abdominal cavity, a fluid instillation matrix associated with the treatment device, a manifold member, a drape, a negative-pressure source fluidly connected to the treatment device, and a fluid source fluidly connected to the fluid instillation matrix. The treatment device may include a plurality of fluid removal pathways. The fluid instillation matrix may include a plurality of fluid delivery pathways. The manifold member may be positioned adjacent to a central portion of the treatment device. The drape may be adapted to form a fluid seal around the treatment device, the fluid instillation matrix, and the manifold member.

In other embodiments, a dressing for treating a tissue site may include a protective layer, a fluid distribution hub configured to exchange fluid with the tissue site, and a plurality of treatment tubes. Each of the plurality of treatment tubes may include a first conduit adapted to deliver fluid from the fluid distribution hub to the tissue site and a second conduit adapted to transport fluid to the fluid distribution hub.

In additional embodiments, a system for treating a tissue site may include an occlusive layer, a fluid removal manifold, and a fluid distribution vessel. The fluid removal manifold may be positioned adjacent a first surface of the occlusive layer, and the fluid distribution vessel may be positioned adjacent a second surface of the occlusive layer.

In yet additional embodiments, a device for treating a tissue site may include a film layer having a first side and a second side, a fluid collection chamber, a fluid distribution chamber, and a conduit. The fluid collection chamber may be formed by a second film layer welded to the first side of the film layer. The fluid distribution chamber may be formed by a third film layer welded around a perimeter to the second side of the film layer and comprising an interface for fluid connection to a conduit. The conduit may extend from the fluid collection chamber through an aperture in the film layer and through the fluid distribution chamber to the interface.

In still additional embodiments, a system for treating a tissue site in an abdomen may include a dressing member, a fluid delivery vessel, and a drape. The dressing member may include a plurality of fluid pathways configured to communicate negative pressure to the tissue site. The fluid delivery vessel may be adapted to be positioned adjacent a first surface of the dressing member and may include a first side having a plurality of openings for delivering fluid to the tissue site. The drape may be adapted to be placed over a second surface of the plurality of fluid pathways.

Objectives, advantages, and a preferred mode of making and using the claimed subject matter may be understood best by reference to the accompanying drawings in conjunction with the following detailed description of illustrative embodiments.

BRIEF DESCRIPTION OF THE DRAWINGS

FIG. 4B is a schematic, side view of a portion of the illustrative embodiment of an abdominal treatment device of FIG. 4A;

FIGS. 7A-7C are schematic, plan views of additional illustrative embodiments of an abdominal treatment device that may be associated with the therapy system of FIG. 1;

FIGS. 10A-10C are schematic diagrams of another illustrative embodiment of an abdominal treatment device that may be associated with the therapy system of FIG. 1;

FIGS. 11A-11B are schematic diagrams of another illustrative embodiment of an abdominal treatment device that may be associated with the therapy system of FIG. 1;

FIGS. 13A-13B are schematic diagrams, with portions in cross-section, of another illustrative embodiment of an abdominal treatment device that may be associated with the therapy system of FIG. 1;

FIGS. 14A-14B are schematic diagrams, with portions in cross-section, of another illustrative embodiment of an abdominal treatment device that may be associated with the therapy system of FIG. 1;

FIG. 16 is a schematic diagram, with a portion in cross-section, of a portion of the illustrative embodiment of an abdominal treatment device of FIG. 15, according to some embodiments;

FIG. 17 is a schematic diagram, with a portion in cross-section, of a portion of the illustrative embodiment of an abdominal treatment device of FIG. 15, according to some additional embodiments;

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
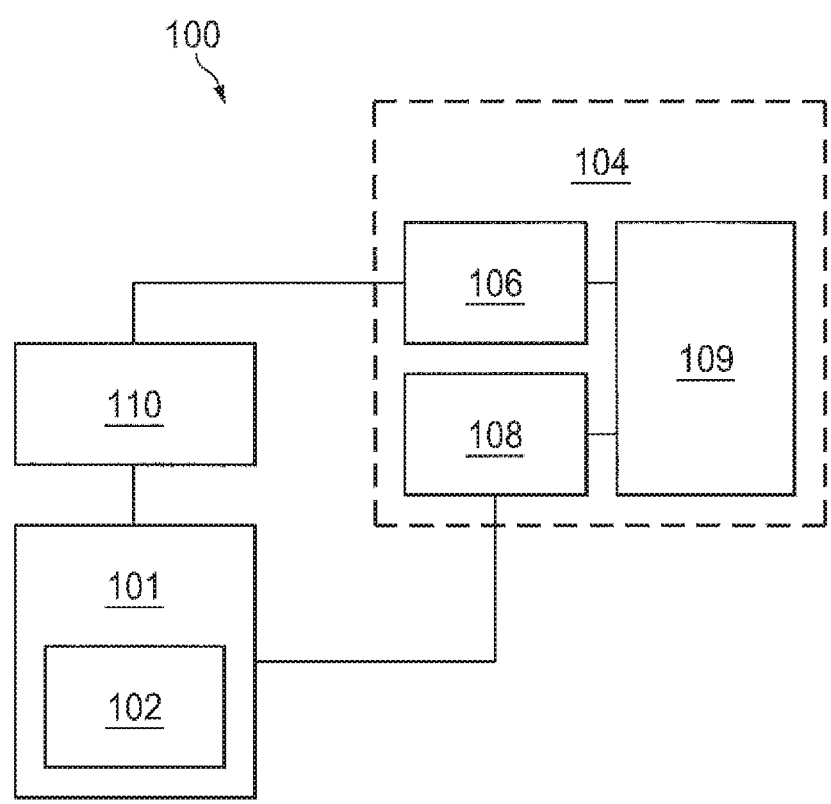
FIG. 1 is a functional block diagram of an example embodiment of a therapy system that can deliver negative pressure as well as a treatment fluid to a tissue site and can manage fluids in accordance with this specification.

FIG. 1 is a simplified functional block diagram of an example embodiment of a therapy system 100 that can provide negative-pressure therapy along with instillation of topical treatment solutions in accordance with this specification. The therapy system may be applied to a human patient, as well as used on other types of subjects. The therapy system 100 may include a treatment device 101 including a dressing 102, and a therapy unit 104. In some embodiments, the therapy unit 104 may include a negative-pressure source, such as negative-pressure source 106, a fluid source, such as fluid source 108, and a controller 109. In other embodiments, the therapy unit 104 may include the negative-pressure source 106, while the fluid source 108 and/or the controller 109 may be freestanding, separate units. The therapy system 100 may also include additional components such as a container 110, which may also be in fluid communication with the treatment device 101, dressing 102, and the therapy unit 104.

Components of the therapy system 100 may be fluidly coupled to each other to provide a path for transferring fluids (i.e., liquid and/or gas) between the components. For example, components may be fluidly coupled through a fluid conductor, such as a tube. A "tube," as used herein, broadly includes a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may also be coupled by virtue of physical proximity, being integral to a single structure, or being formed from the same piece of material. Moreover, some fluid conductors may be molded into or otherwise integrally combined with other components. Coupling may also include mechanical, thermal, electrical, or chemical coupling (such as a chemical bond) in some contexts. For example, a tube may mechanically and fluidly couple the treatment device 101 to the therapy unit 104 in some embodiments. In general, components of the therapy system 100 may be coupled directly or indirectly.

The therapy system 100 may include a negative-pressure supply, such as negative-pressure source 106, which may be configured to be coupled to a distribution component, such as a dressing. In general, a distribution component may refer to any complementary or ancillary component configured to be fluidly coupled to a negative-pressure supply in a fluid path between a negative-pressure supply and a tissue site. A distribution component is preferably detachable, and may be disposable, reusable, or recyclable. For example, the dressing 102 of the treatment device 101 may be fluidly coupled to the negative-pressure source 106 of the therapy unit 104, as illustrated in FIG. 1. In some embodiments, the treatment device 101 may include a dressing 102, as well as additional tissue interfaces, fluid conduits, and/or a cover. In some embodiments, a dressing interface may facilitate coupling the negative-pressure source 106 to the dressing 102 of the treatment device 101. For example, such a dressing interface may be a SENSAT.R.A.C.™ Pad available from KCI of San Antonio, Tex.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the treatment device 101. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

A negative-pressure supply, such as the negative-pressure source 106 of the therapy unit 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. A negative-pressure supply may also have one or more supply ports configured to facilitate coupling and de-coupling the negative-pressure supply to one or more distribution components.

The therapy system 100 may also include a source of instillation solution. For example, a fluid source 108 may be fluidly coupled to the treatment device 101, and thus the dressing 102, as illustrated in the example embodiment of FIG. 1. The fluid source 108 may be fluidly coupled to a positive-pressure source in some embodiments, or may be fluidly coupled to the negative-pressure source 106. A regulator, such as an instillation regulator, may also be fluidly coupled to the fluid source 108 and the treatment device 101.

A fluid source, such as the fluid source 108, may be housed within or used in conjunction with other components to facilitate movement of a fluid. The fluid source 108 may be a fluid pump, for example a peristaltic pump. Alternatively, in some embodiments, the fluid source 108 may be a fluid reservoir, which may store and deliver fluid. In any embodiment, the fluid source 108, such as a fluid pump or a fluid reservoir, may include a container, such as a canister, pouch, or other storage component.

The fluid source 108 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

A controller, such as the controller 109, may be a microprocessor or computer programmed to operate one or more components of the therapy system 100, such as the negative-pressure source 106 and the fluid source 108. In some embodiments, for example, the controller 109 may be a microcontroller, which generally comprises an integrated circuit containing a processor core and a memory programmed to directly or indirectly control one or more operating parameters of the therapy system 100. Operating parameters may include the power applied to the negative-pressure source 106, the pressure generated by the negative-pressure source 106, or the pressure distributed to the treatment device 101, for example. Additional operating parameters may include the power applied to the fluid source 108, flow rate of instillation fluid provided by the fluid source 108, or volume of fluid distributed to the treatment device 101. The controller 109 is also preferably configured to receive one or more input signals, such as a feedback signal, and programmed to modify one or more operating parameters based on the input signals.

The container 110 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

The term "tissue site" in this context broadly refers to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted.

In some embodiments, the negative-pressure source 106, fluid source 108, controller 109, and container 110 may be integrated within a single therapy unit, such as therapy unit 104. For example, the therapy system 100 may therefore include the treatment device 101 along with a therapy unit 104 such as a V.A.C.ULTA™ therapy unit, V.A.C.IN-STILL™ wound therapy system, INFOV.A.C.™ therapy unit, or other suitable therapy units. For example, in some embodiments, the therapy unit 104 may comprise or consist essentially of a V.A.C.ULTA™ unit, which may include software modules specific to negative-pressure therapy in combination with fluid instillation therapy, and specific for use with abdominal dressing systems, such as embodiments of the treatment device 101. Alternatively, any other device capable of providing intermittent negative-pressure therapy may be suitable along with any mechanical fluid instillation device, or any negative-pressure therapy device in combination with a manually-managed fluid instillation source, such as a gravity-fed fluid vessel, manual fluid pump, or monitored IV bag or bottle.

Figure 2:
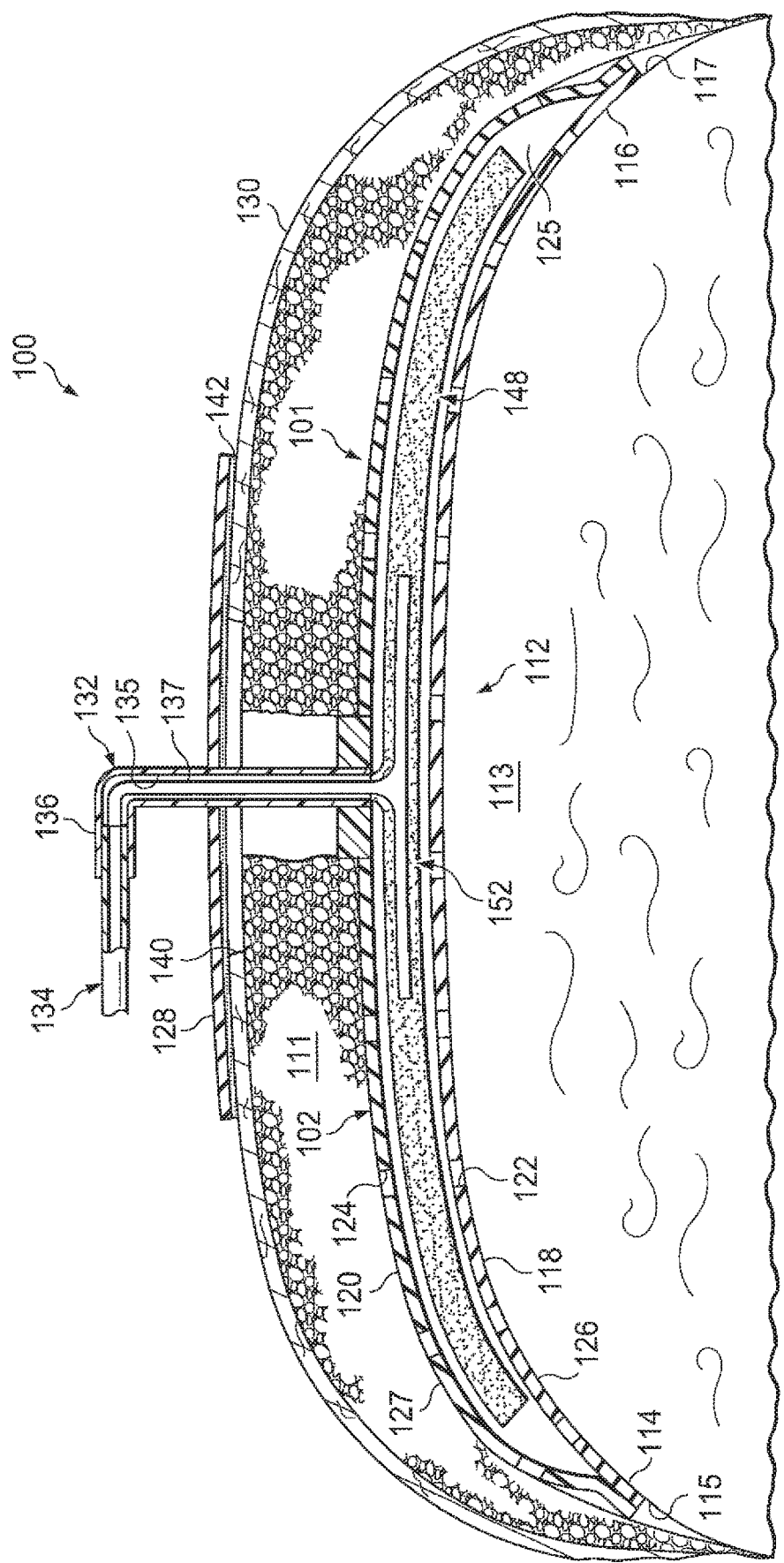
FIG. 2 is a schematic diagram, with a portion in cross-section, of an illustrative device for treating an abdominal cavity that may be associated with some embodiments of the therapy system of FIG. 1.

Referring now primarily to FIG. 2, an illustrative embodiment of a treatment device 101 for treating an abdominal cavity 111 is presented. The treatment device 101 may be for treating a tissue site 112. In this illustrative embodiment, the tissue site 112 may include tissue in a body cavity, and in particular, the abdominal cavity 111. The tissue site 112 may include the abdominal contents 113 or tissue that is proximate the abdominal cavity 111. Treatment of the tissue site 112 may include removal of fluids, e.g., ascites, protection of the abdominal cavity, or negative-pressure therapy.

The illustrative systems and devices herein may allow for the irrigation and washing out of an abdominal cavity, such as the abdominal cavity 111, with the controlled and regulated introduction of fluid. In some instances, it may be necessary to wash or cleanse a contaminated abdominal cavity as a result of a perforated colon or sepsis. The therapy system 100 can provide means to instill fluid into an open abdomen to cleanse the abdominal contents, including reaching areas such as the small bowel loops, pancreas, etc. Additionally, the treatment device 101 and the therapy system 100 may provide temporary closure to an open abdomen, while removing fluid and reducing edema. Thus, the therapy system 100 may provide the capability of performing washouts of a tissue site, such as abdominal cavity 111, without having to repeatedly remove one or more dressings applied to the tissue site of a patient or bringing the patient into the operating room for manual fluid introduction procedures. The therapy system 100 may thus be able to provide a controlled and regulated full abdominal wash, as well as have the capability to provide a targeted wash to certain areas within the abdomen when required. The disclosed embodiments may also provide support and maintenance of the fascial domain of an abdominal cavity, such as abdominal cavity 111, and provide overall protection to the abdominal contents.

As shown in FIG. 2, the treatment device 101 may include a dressing 102, which may be disposed within the abdominal cavity 111 of a patient to treat the tissue site 112. The dressing 102 may be supported by the abdominal contents 113. As depicted, a first dressing portion 114 of the dressing 102 may be positioned in or proximate to a first paracolic gutter 115, and a second dressing portion 116 may be placed in or proximate to a second paracolic gutter 117. The first paracolic gutter 115 and the second paracolic gutter 117 may each be, for example, an open space on opposing sides of the abdominal cavity 111 among the abdominal contents 113. The first paracolic gutter 115 may be laterally disposed from the second paracolic gutter 117 or otherwise positioned on an opposite side of the tissue site 112 from the second paracolic gutter 117. Although FIG. 2 depicts the treatment device 101 deployed at the abdominal cavity 111, the treatment device 101 and therapy system 100 may be used at other types of tissue sites.

The dressing 102 may be formed with a plurality of liquid-impermeable layers, e.g., a first liquid-impermeable layer 118 and a second liquid-impermeable layer 120. The plurality of liquid-impermeable layers, e.g., first liquid-impermeable layer 118 and second liquid-impermeable layer 120, are formed with fenestrations 122 and 124, respectively. "Liquid impermeable" with respect to "liquid-impermeable layers" means that the layers are formed with a liquid-impermeable material. Thus, although formed with a liquid-impermeable material, the layer may be liquid permeable when fenestrated, but nonetheless is referred to as a liquid-impermeable layer. The fenestrations 122 and 124 may take many shapes or combinations of shapes, including circular apertures, rectangular openings, or polygons, for example. The fenestrations 122 and 124 are presented in this illustrative embodiment as slits, or linear cuts. In some embodiments, the first liquid-impermeable layer 118 and the second liquid-impermeable layer 120 may be sealingly coupled to one another in any suitable manner, such as, without limitation, by welding, bonding, adhesives, cements, or other bonding devices. The first liquid-impermeable layer 118 may be adapted to be positioned between the second liquid-impermeable layer 120 and the tissue site 112 and/or abdominal contents 113. In the example embodiment of FIG. 2, a chamber 125 is formed between at least two layers of the plurality of liquid-impermeable layers, e.g., the first liquid-impermeable layer 118 and the second liquid-impermeable layer 120. The dressing 102 has a first side 126 and a second side 127. The first liquid-impermeable layer 118 and the second liquid-impermeable layer 120 may comprise a non-adherent material, such as a medical drape, capable of inhibiting tissue from adhering to the medical drape. For example, in some embodiments, the first liquid-impermeable layer 118 and the second liquid-impermeable layer 120 may comprise a breathable polyurethane film. In some embodiments, the chamber 125 formed between the liquid-impermeable layers 118 and 120 may include a fluid removal assembly 148 for communicating negative pressure and removing fluids, such as exudates from the tissue site 112, as well as an instillation matrix 152 for delivering instillation fluid to the tissue site 112.

In some embodiments, the therapy system 100 may further include a sealing member 128 for providing a fluid seal over the abdominal cavity 111. Additionally, one or more skin closure devices may be placed on an epidermis 130 of a patient. In some embodiments, the therapy system 100 may also include an interface 132 for fluidly connecting the dressing 102 and other portions of the treatment device 101 to a conduit 134. The interface 132 may include a connector 136. Alternatively, the interface 132 may be partially or fully embedded within a portion of the dressing 102, or configured in any other way possible for fluidly connecting the treatment device 101 to a therapy unit, such as the therapy unit 104 of FIG. 1. The conduit 134 may be fluidly coupled to negative-pressure source 106 and/or fluid source 108 of the therapy unit 104 for providing negative pressure and/or treatment fluid, respectively, to the treatment device 101. In some embodiments, the conduit 134 may include two substantially parallel, fluidly-isolated conduits, one of which for fluidly coupling the treatment device 101 to the negative-pressure source 106 and the other for fluidly coupling the treatment device 101 to the fluid source 108. Thus, in some embodiments, the conduit 134 may be a multi-lumen conduit with both a negative-pressure lumen 135 and a fluid supply lumen 137. In some other illustrative embodiments, the conduit 134 may be replaced with two separate conduits, one containing a negative-pressure lumen and the other containing a fluid supply lumen.

In some embodiments, the sealing member 128 may provide a bacterial barrier and protection from physical trauma. The sealing member 128 may also be constructed from a material that can reduce evaporative losses and provide a fluid seal between two components or two environments, such as between a therapeutic environment and a local external environment. The sealing member 128 may be, for example, an elastomeric film or membrane that can provide a seal adequate to maintain a negative pressure at a tissue site for a given negative-pressure source. The sealing member 128 may have a high moisture-vapor transmission rate (MVTR) in some applications. For example, the MVTR may be at least 300 $g/m^2$ per twenty-four hours in some embodiments. In some example embodiments, the sealing member 128 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device, such as attachment device 142, may be used to attach the sealing member 128 to an attachment surface, such as the epidermis 130 of the patient. The attachment device 142 may also be used to attach the sealing member 128 to a gasket, or another sealing member or cover. The attachment device may take many forms. For example, an attachment device may be a medically-acceptable, pressure-sensitive adhesive that extends about a periphery, a portion, or an entire sealing member. In some embodiments, for example, some or all of the sealing member 128 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

Although not necessarily depicted in FIG. 2, in some embodiments, the therapy system 100 may further include a filler material, such as a portion of foam, that is placed between the second liquid-impermeable layer 120 and the sealing member 128. The filler material may be sized to fill the portion of abdominal volume beneath or surrounding an incision or opening into abdomen from the skin layers, such as a portion of abdominal cavity 111. In some embodiments, the filler material may serve as a distribution manifold for negative pressure. For example, in some embodiments, the filler material may be positioned between the second liquid-impermeable layer 120 and the sealing member 128, and a negative pressure lumen or conduit, such as negative-pressure lumen 135, may be pneumatically connected to the sealing member 128. As a result, fluid removal may occur from the layers of the treatment device 101 through the filler material positioned atop second liquid-impermeable layer 120, and into the negative-pressure lumen 135. In some embodiments, the filler material may include an open-cell, reticulated polyurethane foam such as GRANUFOAM™ dressing, available from Kinetic Concepts, Inc. of San Antonio, Tex.

Figure 3:
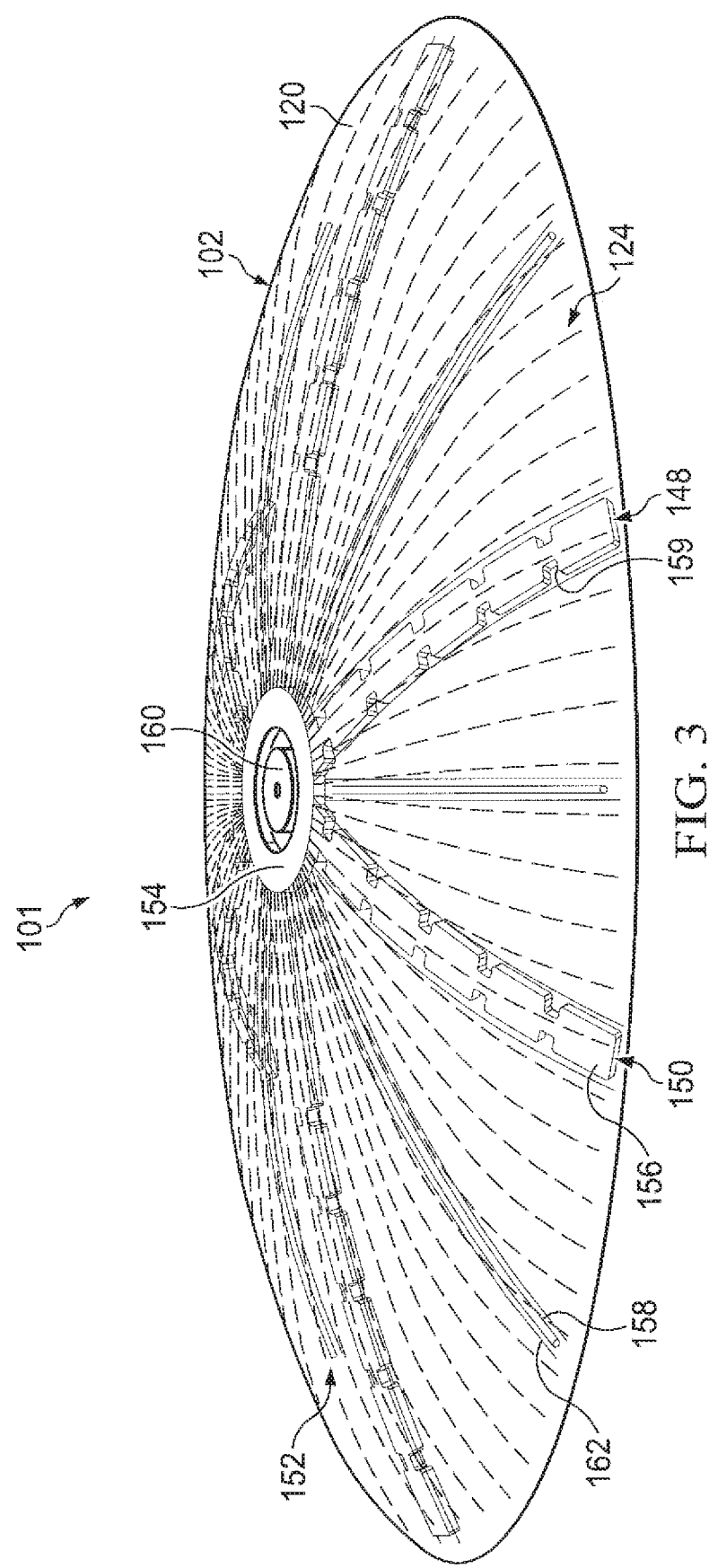
FIG. 3 is a schematic, plan view of an illustrative embodiment of an abdominal treatment device that may be associated with some embodiments of the therapy system of FIG. 1.

Referring now primarily to FIG. 3, the treatment device 101 may be adapted to provide negative pressure from the negative-pressure source 106 of the therapy unit 104 to a tissue site, such as tissue site 112 of the abdominal cavity 111 of FIG. 2, and to collect and transport fluid extracted from the tissue site 112. Additionally, the treatment device 101 may also be adapted to deliver a fluid, such as a treatment fluid or medicament, from the fluid source 108 of the therapy unit 104 to the tissue site 112. As discussed with respect to FIG. 2, in some embodiments, the dressing 102 of the treatment device 101 may include multiple liquid-impermeable layers, or visceral protective layers, which protect the underlying abdominal contents 113 of the tissue site 112. For example, in some embodiments, the dressing 102 may include a first liquid-impermeable layer 118 and a second liquid-impermeable layer 120, which are formed from a polyurethane material, with each of the liquid-impermeable layers measuring between 20 and 400 micrometers in thickness. As shown in FIG. 3, one or both of the liquid-impermeable layers, such as second liquid-impermeable layer 120 may include fenestrations 124 for promoting fluid removal throughout an abdominal cavity 111.

As illustrated in FIG. 3, some embodiments of the treatment device 101 may also include a fluid removal assembly 148 and an installation matrix 152. For example, in some embodiments, the fluid removal assembly 148 may include a plurality of fluid removal pathways 150, each of which is fluidly coupled to a fluid removal hub 154. The fluid removal hub 154 may serve as a distribution mechanism for communicating negative pressure to each of the fluid removal pathways 150 from the interface 132 and the negative-pressure source 106. The fluid removal pathways 150 may take the form of numerous different shapes or be formed from a variety of materials. For example, in some embodiments, the fluid removal pathways 150 may be formed from portions of the first liquid-impermeable layer 118 and the second liquid-impermeable layer 120 that have been welded together to form channels. Alternatively or additionally, the fluid removal pathways 150 may comprise or consist essentially of folds or pleats in either or both of the liquid-impermeable layers 118 and 120. Other example embodiments of fluid removal pathways 150 may include channels formed by extruded materials, channels embossed onto the liquid-impermeable layers 118 and 120, or separate tubing material forming individual tubes for use as the fluid removal pathways 150. Multi-lumen tubes may also be used for the fluid removal pathways 150. In various embodiments, each of the different forms and configurations of fluid removal pathways 150 may also apply to fluid delivery tubes of the installation matrix 152, as suitable.

In some embodiments, each of the fluid removal pathways 150 may include a manifold member, such as manifold member 156, for communicating negative pressure and drawing fluids though the fluid removal pathways 150. For example, in some embodiments, each manifold member 156 may be a single piece of manifold member material that runs the length of the fluid removal pathway 150, while some embodiments include manifold members 156 that are made of discrete portions or sections of manifold member material. In either case, the manifold member 156 may include a series of indentations 159, which may assist with conformability, including sizing and flexibility, of the manifold member 156 and the fluid removal pathways 150, as well as the communication of negative pressure and/or collected fluids.

The manifold member 156 may generally include any substance or structure that is provided to assist in applying negative pressure to, delivery fluids to, or removing fluids from the tissue site 112 or other location. The manifold member 156 may typically a manifold member material having a plurality of flow channels or pathways that distribute the fluids provided to and removed around the manifold member 156. For example, a manifold member material may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be interconnected to improve distribution or collection of fluids across a tissue site. In some illustrative embodiments, a manifold may be a porous foam material having interconnected cells or pores. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, a manifold may additionally or alternatively comprise projections that form interconnected fluid pathways. For example, a manifold may be molded to provide surface projections that define interconnected fluid pathways.

In some embodiments, the manifold member 156 includes a porous foam and includes a plurality of interconnected cells or pores that act as flow channels. The average pore size of a foam may vary according to needs of a prescribed therapy. For example, in some embodiments, the manifold member 156 may be a foam having pore sizes in a range of 400-600 microns. The tensile strength of the manifold member 156 may also vary according to needs of a prescribed therapy. For example, the tensile strength of a foam may be increased for instillation of topical treatment solutions. In some embodiments, the manifold member 156 may include a polyurethane foam which may be between 6 mm and 10 mm in thickness. In one non-limiting example, the manifold member 156 may be an open-cell, reticulated polyurethane foam such as GRANUFOAM™ dressing or V.A.C. VERAFLO™ dressing, both available from Kinetic Concepts, Inc. of San Antonio, Tex. Some embodiments may include a manifold member 156 having additional layers or materials, such as absorptive materials, wicking materials, hydrophobic materials, and hydrophilic materials.

The installation matrix 152 may include a plurality of fluid delivery tubes 158 and a distribution hub 160. The components of the installation matrix 152 may be constructed of a variety of different materials. For example, some or all of the components of the installation matrix 152 may be constructed of soft, medical-grade silicone or PVC tubing material. The plurality of fluid delivery tubes 158 may vary in size, based on the particular size and application of the treatment device 101, as well as the conditions of the tissue site 112 to which the treatment device 101 is to be applied. For example, the fluid delivery tubes 158 may each have an inner diameter of between 0.5 mm and 4 mm. In some embodiments, the fluid delivery tubes 158 may each have an inner diameter of between 1 mm and 2 mm. The rather small size of the fluid delivery tubes 158 may be conducive for avoiding patient discomfort during therapy as well as ease of removal of the treatment device 101 following completion of therapy.

As shown in FIG. 3, but also referring again to FIG. 2, in some embodiments, the instillation matrix 152 may be substantially encapsulated within multiple layers of the dressing 102. For example, the fluid delivery tubes 158 may be positioned with the chamber 125 formed by the first liquid-impermeable layer 118 and the second liquid-impermeable layer 120, along with the fluid removal pathways 150. In some instances, the instillation matrix 152, along with the fluid removal pathways 150, may be inserted into the chamber 125 between the first liquid-impermeable layer 118 and the second liquid-impermeable layer 120 at the time of manufacture, before the liquid-impermeable layers 118 and 120 are attached together, for example by ultrasonic welding. Each of the fluid removal pathways 150 and the fluid delivery tubes 158 may be secured in place between the liquid-impermeable layers 118 and 120 by welding the liquid-impermeable layers 118 and 120 together along borders of the fluid removal pathways 150 and fluid delivery tubes 158, as shown by weld lines 162.

Figure 4A:
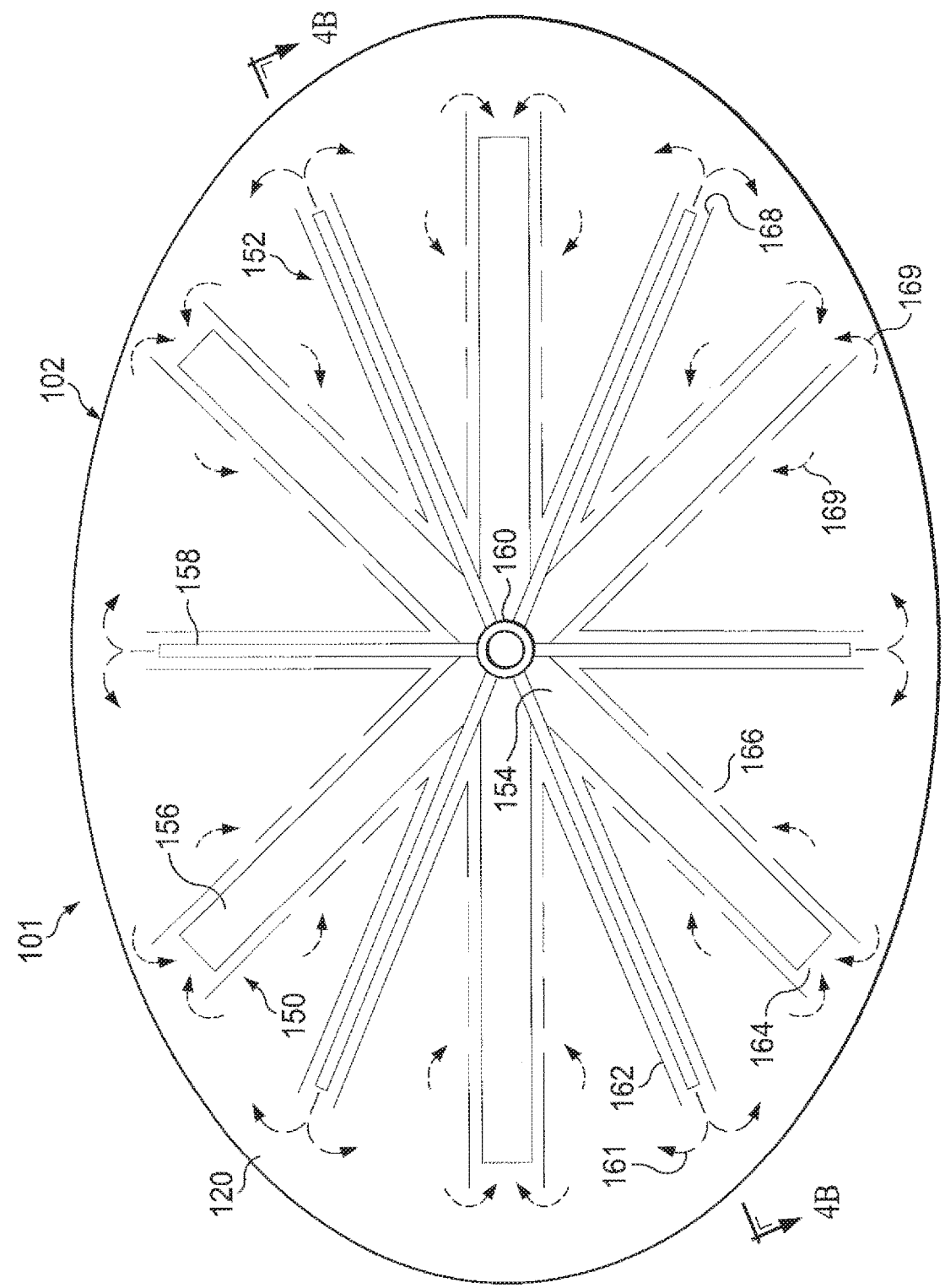
FIG. 4A is a schematic, plan view of an illustrative embodiment of a portion of an abdominal treatment device.

Referring now primarily to FIGS. 4A-4B, additional features that may be associated with some example embodiments of the treatment device 101 of FIG. 3 are shown. For example, as shown in FIG. 4A, each fluid removal pathway 150 may include open ends 164 as well as openings or apertures, such as removal pathway apertures 166, along the length of the fluid removal pathway 150. Thus, in such embodiments, the fluid removal pathways 150 may communicate negative pressure and draw fluids through both the ends as well as along the lengths of the fluid removal pathways 150. Meanwhile, in this example embodiment, the fluid delivery tubes 158 may only have open ends, such as delivery ends 168, and may otherwise be fluidly isolated from the surroundings along the length of the fluid delivery tubes 158. In some embodiments, the treatment device 101 may be offered in a single size with the option to cut and remove portions of the treatment device 101 to reduce its size, thus potentially shortening the length of the fluid delivery tubes 158, as required on an individual patient basis. Thus, by having openings of the fluid delivery tubes 158 only at the ends of the individual tubes, greater levels of customization may be achieved since the fluid delivery tubes 158 and overall instillation matrix 152 do not rely on a set length of the fluid delivery tubes 158 or number or size of perforations along the fluid delivery tubes 158 to evenly distribute instillation fluid.

Figure 5:
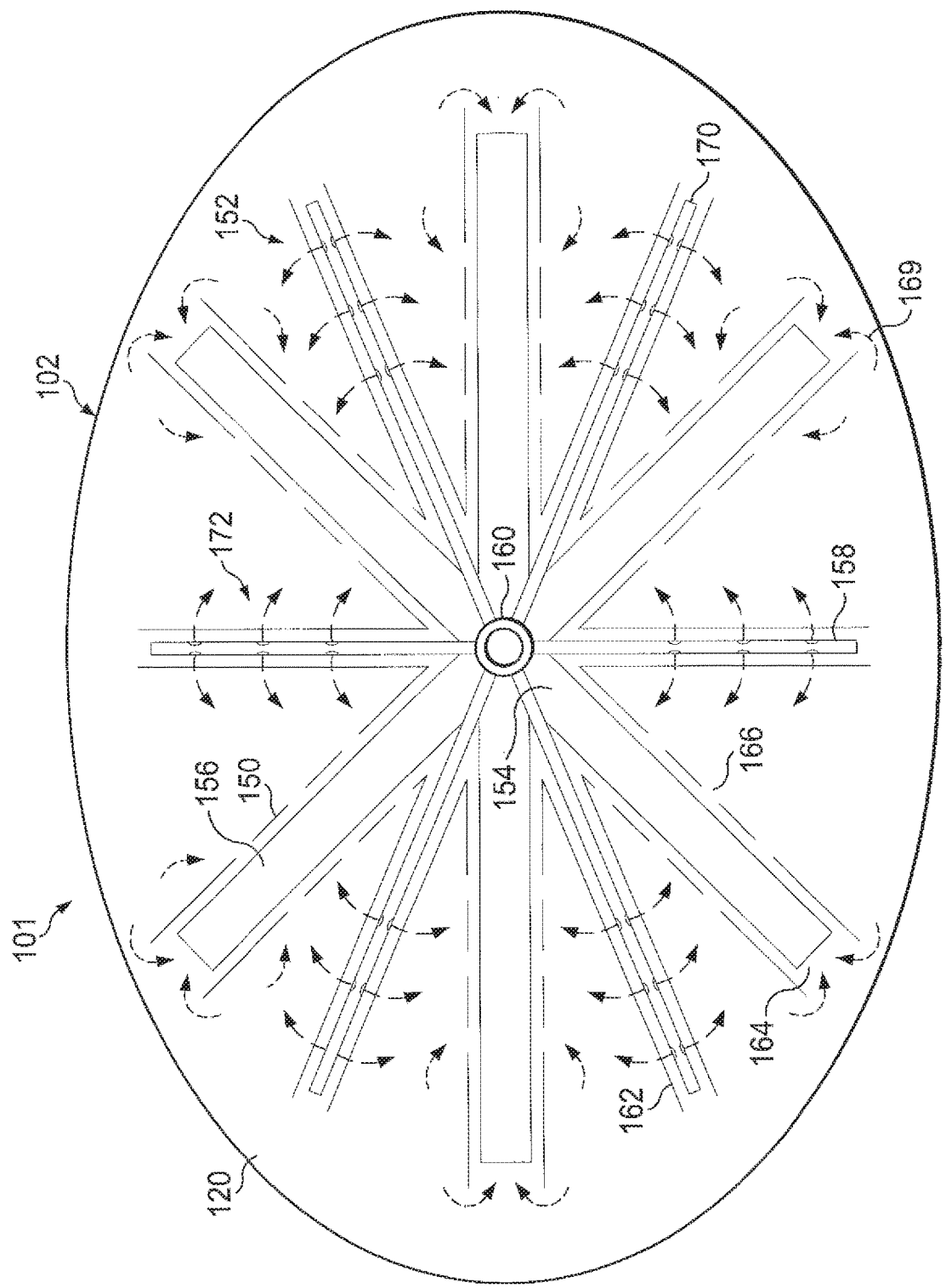
FIG. 5 is a schematic, plan view of a portion of an abdominal treatment device, according to another illustrative embodiment.

FIG. 5 shows additional features that may be associated with some example embodiments of the treatment device 101 of FIG. 3. The components and features of the example treatment device 101 of FIG. 5 are largely the same or similar to those of the embodiment of the treatment device 101 shown in FIG. 4 (collectively), with the exception of certain aspects of the fluid delivery tubes 158. For example, as shown in FIG. 5, rather than having open ends, such as delivery ends 168 of FIG. 4, for delivering instillation fluid to a tissue site, the fluid delivery tubes 158 may instead have closed ends, such as delivery tube closed ends 170. Instead, each of the fluid delivery tubes 158 may include openings or perforations, such as delivery tube perforations 172, along its length. However, the embodiments shown in FIGS. 4 and 5 are for illustrative purposes only, and it is also contemplated that the fluid delivery tubes 158 may include both open ends as well as perforations along their lengths.

The instillation matrix 152 may be adapted to deliver fluids across the tissue site 112 in a substantially uniform manner. For example, each of the fluid delivery tubes 158, the delivery ends 168, and the delivery tube perforations 172 may be adapted to provide substantially the same back-pressure. Such a configuration may prevent fluid from traveling more freely through or otherwise favoring one of the fluid delivery tubes 158 over another of the fluid delivery tubes 158. Herein, back-pressure may refer to an increase in localized pressure caused by a resistance to fluid flow, such as through the confined space of a lumen or aperture. Back-pressure may result from the geometric configuration and material properties of the confined space, such as, without limitation, the size of the space, the presence and shape of bends or joints in the space, surface finishes within the space, and other characteristics. In some embodiments, a fluid hub, such as distribution hub 160, may not be required if the perforations along the lengths of the fluid delivery tubes 158, such as delivery tube perforations 172, are sized to provide a substantially even distribution of fluid throughout the abdomen.

Fluids tend to follow a path of least resistance, and thus, poor fluid distribution may result from one of the fluid delivery tubes 158 having less back-pressure or resistance to fluid flow than another of the fluid delivery tubes 158. Similarly, poor fluid distribution may result from one of the fluid delivery apertures, such as the delivery ends 168 or delivery tube perforations 172, having less back-pressure or resistance to fluid flow than another of the fluid delivery apertures. Consistency among the size and configuration of the fluid delivery tubes 158, and the number and size of the delivery ends 168 and delivery tube perforations 172 in each of the fluid delivery tubes 158, for example, may enhance the uniformity of fluid delivery to the tissue site 112. Thus, in some embodiments, the delivery apertures, such as the delivery ends 168 and the delivery tube perforations 172, may be substantially equal in number and size on each of the fluid delivery tubes 158. Further, each of the fluid delivery tubes 158 may have substantially the same dimensions.

For example, in some embodiments, the fluid delivery tubes 158 may have a cylindrical tube shape and may have an internal diameter between about 2 millimeters and about 6 millimeters. Further, in some embodiments, the fluid delivery tubes 158 may have an internal diameter of about 4 millimeters. In some other embodiments, the fluid delivery tubes 158 may have an alternate tubing profile, where a lower-profile, or "flatter" tubing profile may be used to increase user comfort when the treatment device 101 is in place in a tissue site 112. The delivery apertures, such as the delivery ends 168 and the delivery tube perforations 172, in some embodiments, may have a diameter between about 0.1 millimeters and about 0.8 millimeters. Sizing the internal diameter or cross-section of the fluid delivery tubes 158 substantially larger than the size, cross-section, or diameter of the delivery ends 168 and the delivery tube perforations 172 may provide a substantially uniform pressure within each of the fluid delivery tubes 158. In such an embodiment, fluid flow velocity within the fluid delivery tubes 158 may be substantially low or substantially static relative to the high fluid flow velocity through the delivery apertures, such as the delivery ends 168 and the delivery tube perforations 172.

Although not shown in the accompanying figures, in some embodiments, the instillation matrix 152 may include an arrangement of fluid delivery tubes 158 that are arranged in the form of a grid, or "spider web." Thus, in some instances, the instillation matrix 152 may include a plurality of fluid delivery tubes 158 that extend radially from a central hub, as well as additional tubing segments that fluidly connect each of the radially-extending fluid delivery tubes 158. Perforations may exist along any or all portions of the radially-extending fluid delivery tubes 158, as well as the connecting tubing segments.

Figure 6A:
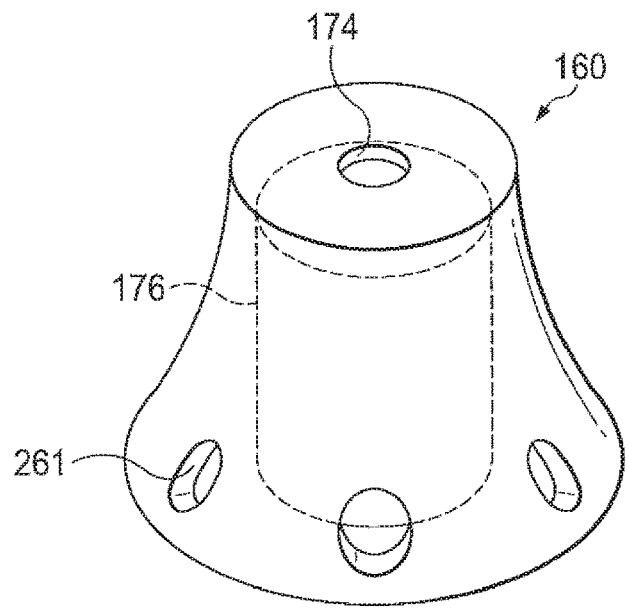
FIG. 6A is a schematic diagram illustrating additional details that may be associated with a portion of an abdominal treatment device of the therapy system of FIG. 1.

FIG. 6A shows a more detailed view of a hub, such as the distribution hub 160 of FIG. 3. In some embodiments, at least a portion of the distribution hub 160 may be positioned between the first liquid-impermeable layer 118 and the second liquid-impermeable layer 120 and may be positioned in fluid communication with the fluid delivery pathways, such as fluid delivery tubes 158. In some embodiments, the height of the distribution hub 160 may be such that the distribution hub 160 may extend outward above a surface of the second liquid-impermeable layer 120 of the treatment device 101. The distribution hub 160 may include a hub port 174, which may be positioned on a top surface of the distribution hub 160. The size and dimensions of the distribution hub 160 may be such that the hub port 174 may be positioned above an upper surface of the second liquid-impermeable layer 120, and may provide fluid communication between a fluid supply lumen of the conduit 134 and the distribution hub 160. In some embodiments, the distribution hub 160 may include a plurality of openings, such as distribution ports 261, positioned around its lower surface. In some embodiments, these distribution ports 261 may be for fluid coupling to the fluid delivery tubes 158 of the instillation matrix 152. The specific size of the openings, or distribution ports 261 may be calibrated to the particular source of instillation fluid, such as fluid source 108, and its specific settings or design parameters. For example, some examples of the fluid source 108 may each require specific sizes of openings due to specific pump flow rates. In some embodiments, the fluid delivery tubes 158 may be positioned circumferentially and substantially symmetrically about the distribution hub 160. Thus, the distribution hub 160 and the fluid delivery tubes 158 may define a fluid instillation pathway.

As shown in FIG. 6A, the distribution hub 160 may comprise a material for assisting with distributing the instillation fluid, such as distribution member 176. The distribution member 176 may include a porous or fluid permeable material, such as, for example, a foam. Further, the distribution hub 160 may be generally elongate and cylindrical in shape or bell-shaped, however may also have other shapes. In other embodiments, the distribution hub 160 may comprise a fitting, such as a tube, tubular fitting, pipe, barbed connection, or similar structure. In such embodiments, the fitting may be pre-bonded or molded directly to the first liquid-impermeable layer 118 or the second liquid-impermeable layer 120 and configured to be fluidly coupled between the fluid supply lumen of the conduit 134 and the fluid delivery tubes 158.

In some embodiments, the distribution hub 160 may be cast or injection molded in a similar soft, medical-grade silicone or PVC material. In some other embodiments, the distribution hub 160 may be fabricated from two sheets of polyurethane film that are welded together. In some additional embodiments, the distribution hub 160 may actually serve as a combined fluid instillation and fluid removal hub, in which case the distribution hub 160 may be fluidly connected to both fluid-delivery as well as fluid-removal conduits of the treatment device 101. In such instances of a combined fluid instillation and fluid removal hub, the distribution hub 160 may include a series of one-way valves. Such one-way valves may be any form of one-way valves, such as off-the-shelf duckbill valves or custom flap valves. These one-way valves may be placed on openings of the distribution hub 160, such as the distribution ports 261, to the fluid delivery tubes 158 and to fluid removal pathways, for example, fluid removal pathways 150. In some embodiments of a combined hub, a common distribution material may be included as part of the hub, while still enabling fluid communication with separate fluid delivery tubes 158 and fluid removal pathways 150.

In some instances, the fluid delivery tubes 158 may be formed separately from the distribution hub 160 and subsequently attached the distribution hub 160 by a medical-grade adhesive or cyclohexanol, or by welding. In other example embodiments, the fluid delivery tubes 158 and the distribution hub 160 of the instillation matrix 152 may be substantially formed as a single structure.

Referring to FIG. 6B, but also again generally to FIG. 2, the interface 132 may provide both a negative-pressure connection as well as a fluid supply connection to the treatment device 101. The interface 132 may be sized, shaped, or otherwise adapted to fluidly connect a negative-pressure lumen 135 and a fluid supply lumen 137 of the conduit 134 to the treatment device 101 in any suitable manner. In some embodiments, the interface 132 may fluidly couple the negative-pressure lumen 135 and the fluid supply lumen 137 through the sealing member 128. For example, one or more sealing member apertures may be disposed through the sealing member 128 to provide fluid communication and access to the components of the treatment device 101 positioned within a sealed space.

In some embodiments, the interface 132 may be formed or molded as part of the negative-pressure lumen 135 and the fluid supply lumen 137. In other embodiments, the negative-pressure lumen 135 and the fluid supply lumen 137 may be, for example, bonded or secured by an interference fit to the interface 132. In some embodiments, a portion of the interface 132, such as a flange, may be coupled to the sealing member 128 for positioning the interface 132 in fluid communication with the treatment device 101 through the sealing member 128. The interface 132 may be coupled to the sealing member 128 in any suitable manner, such as, for example, by an adhesive or other bonding device. For example, in some embodiments, the adhesive for coupling the interface 132 to the sealing member 128 may be the same as that used for the attachment device 142 for the sealing member 128 described above.

Figure 6B:
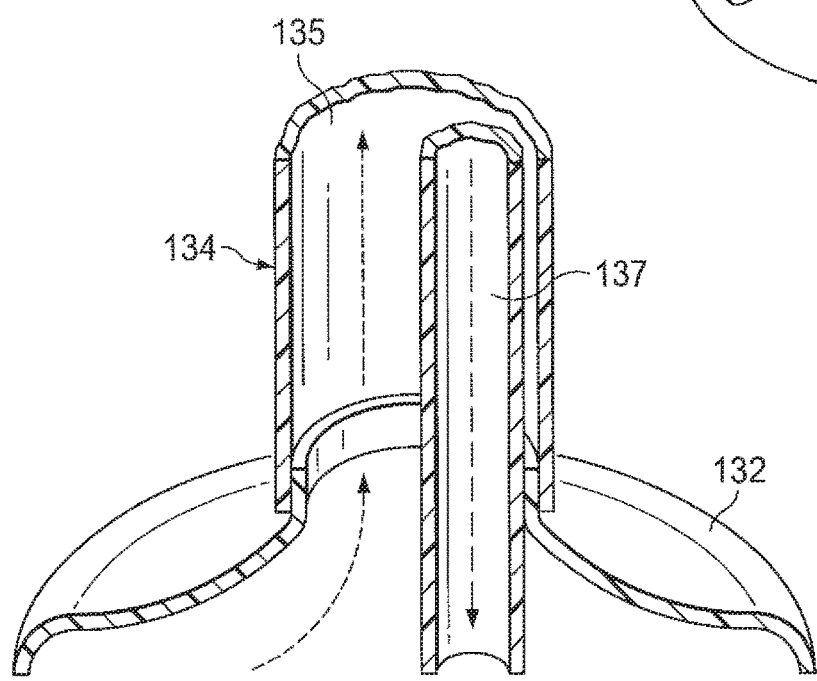
FIG. 6B is a schematic diagram illustrating additional details that may be associated with a portion of the therapy system of FIG. 1.

In some embodiments, as shown in FIG. 6B, the interface 132 may be a multi-port interface providing both the negative-pressure connection and the fluid supply connection as individual, fluidly isolated ports within the multi-port interface, such as interface 132. In such an embodiment, a wall of one of the individual lumens, such as the fluid supply lumen 137 may be coupled to the distribution hub 160 for fluidly isolating the fluid supply connection from the negative-pressure connection. Other configurations for maintaining the fluid isolation of the negative-pressure lumen 135 and the fluid supply lumen 137 are possible.

In other embodiments (not shown), the interface 132 may be a single-port interface that may provide either a negative-pressure connection or a fluid supply connection. Thus, a first single-port interface may provide the negative-pressure connection, and a second single-port interface may provide the fluid supply connection. In other embodiments, the negative-pressure lumen 135 may be fluidly coupled directly to the fluid removal hub 154, and the fluid supply lumen 137 may be fluidly coupled directly to the distribution hub 160 without the interface 132.

In some alternative embodiments, the treatment device 101 may include a fluid hub that may function as both a mechanism for distributing instillation fluid through distribution pathways, as well as distributing negative pressure through, and collecting fluids from, fluid removal pathways. For example, the fluid hub may comprise two layers or chambers separated by a film membrane, such as a polyurethane film membrane. The top layer or chamber may receive and direct clean instillation fluid through a matrix of open pathways to fluid delivery tubes. The top chamber may also include a floor having serrations or pleats to help direct fluid. In some embodiments, the floor may provide a continuous film layer during a fluid instillation phase of therapy, however when under the application of negative pressure, pleats or flaps of the floor may be drawn upwards to provide small openings for fluid to pass through from the lower chamber and upwards out of the fluid hub. The top chamber may also include a porous foam ring around the interior perimeter of the chamber to provide a filter for larger contaminates passing out through the fluid instillation pathways. The foam ring may also function as a seal when compressed under negative pressure, in order to close off the fluid instillation pathways. The lower layer or chamber of the fluid hub may connect to the fluid removal pathways, and the lower chamber may include a manifold material to ensure a fluid pathway remains open under negative pressure. Fluids may be removed from the treatment device 101 and through the fluid hub under the application of negative pressure, with only minimum opportunity for clean instillation fluid and dirty fluids from the tissue site to be mixed. In some embodiments, the fluid hub may include one or more valves in the top chamber, such as O-ring seal valves, which may block off the openings from the top chamber to the fluid instillation pathways, when negative pressure is applied.

Referring generally to FIGS. 1-6B, in some illustrative embodiments of operation of the therapy system 100, the treatment device 101 may be sized to fit the tissue site 112 and disposed at or within the tissue site 112, such as the abdominal cavity 111. If sizing the treatment device 101 is necessary, excess portions of the treatment device 101 may be removed, for example, by cutting or tearing through the first liquid-impermeable layer 118 and second liquid-impermeable layer 120, as well as the fluid removal pathways 150 and fluid delivery tubes 158, of the treatment device 101 for a desired size.

The treatment device 101 may be positioned in contact with the abdominal contents 113, with portions of the treatment device 101 being pushed down into the paracolic gutters of a patient. Specifically, the fluid removal pathways 150 may be positioned or proximate to the first paracolic gutter 115 and the second paracolic gutter 117. When deployed, the treatment device 101 may cover all exposed viscera and may separate the viscera from contact with the walls of the abdominal cavity 111. The treatment device 101 may be sized and shaped to permit such coverage.

The treatment device 101 may be covered at the tissue site 112 with the sealing member 128 to provide a sealed space containing the treatment device 101. The sealing member 128 may be positioned and fluidly sealed about the tissue site 112 with the attachment device 142, as described above. Apertures in the sealing member 128 may be cut or otherwise disposed through the sealing member 128 as necessary, if not already provided as part of the sealing member 128. The negative-pressure connection and the fluid supply connection may be made, for example, with the interface 132 or through direct coupling of the negative-pressure lumen 135 to the fluid removal assembly 148 and the fluid supply lumen 137 to the instillation matrix 152. It is important to note that instillation fluid may be independently fed from a fluid source, such as fluid source 108, through the fluid supply lumen and into the instillation matrix 152. Thus, in some embodiments, the instillation fluid may be fed directly to a fluid hub, such as distribution hub 160, and therefore, the fluid instillation and fluid removal pathways may be controlled as separate entities. Thus, potential contamination of clean fluid instillation pathways may be reduced or largely eliminated, and a more efficient cleansing cycle may be obtained. Depending on how the components of the treatment device 101 are specifically configured, in some embodiments, fluid may be fed through the fluid instillation tubing directly into low points of an abdomen, such as the paracolic gutters, for example, first paracolic gutter 115 and second paracolic gutter 117.

Activating the negative-pressure source 106 may provide negative pressure to the fluid removal assembly 148 through the negative-pressure lumen 135 of the conduit 134. The fluid source 108 may provide instillation fluid to the instillation matrix 152 through the fluid supply lumen 137, for example, by activing a pump or positive-pressure source in the fluid source 108, or by operation of gravitational or manual user forces acting on the instillation fluid. Negative pressure and instillation fluid may be provided to the treatment device 101 simultaneously, or cyclically, at alternate times. Further, negative pressure and instillation fluid may be applied to the treatment device 101 intermittently or continuously.

When the negative-pressure source 106 is activated, the negative-pressure lumen 135 of the conduit 134 may distribute the negative pressure to the fluid removal hub 154 and to the fluid removal pathways 150 of the fluid removal assembly 148. As shown in FIGS. 4A-5 by the extraction arrows 169, fluid from the tissue site 112 may be drawn or extracted through the open ends 164 and removal pathway apertures 166 into the fluid removal pathways 150. Fluid in the fluid removal pathways 150 may be communicated through the fluid removal pathways 150 and into the fluid removal hub 154, where the fluid may be drawn into the negative-pressure lumen 135 of the conduit 134 and ultimately into the container 110.

When the fluid source 108 is activated or instillation fluid is otherwise being delivered to the treatment device 101, the instillation fluid may pass into the distribution hub 160 of the instillation matrix 152. From the distribution hub 160, the instillation fluid may be communicated to the tissue site 112 through the fluid delivery tubes 158 and the delivery ends 168 and/or delivery tube perforations 172 in the fluid delivery tubes 158, as shown by arrows 161. The configuration of the instillation matrix 152 and the associated back-pressure as described above may facilitate delivery of the instillation fluid to the tissue site 112 in a substantially uniform manner.

Fluid being instilled or delivered to the tissue site 112 through the instillation matrix 152 may remain physically and fluidly separate from the fluid removal assembly 148 until reaching or coming into direct contact with the tissue site 112. Once delivered to the tissue site 112, the instillation fluid may become comingled with, for example, previously instilled fluids, wound fluid, tissue fluids, and other fluids that may be considered waste fluid. When negative pressure is being applied to the treatment device 101, tissue or wound fluids from the tissue site 112 and any instillation fluid previously delivered to the tissue site 112 may be extracted through the separate fluid removal assembly 148. Fluid being extracted from the tissue site 112 through the fluid removal assembly 148 may remain physically and fluidly separate from the instillation matrix 152. Such separation between the fluid removal assembly 148 and the instillation matrix 152 may prevent fluids that may remain, for example, in the fluid removal pathways 150 or the fluid removal hub 154, after or during extraction from the tissue site 112, from being forced back into the tissue site 112 during fluid instillation.

Further, the separation of the fluid removal assembly 148 from the instillation matrix 152 may promote efficient use of instillation fluid. For example, as described above, the fluid removal hub 154 and the fluid removal pathways 150 may comprise a porous, fluid permeable material, such as a foam. This fluid permeable material may include fluid flow passageways that may remain open or fluid permeable while under negative pressure for extracting fluid from the tissue site 112. Further, fluid extracted from the tissue site 112 may be stored within the fluid removal assembly 148 of the treatment device 101 before being drawn into the negative-pressure lumen 135. The capability to provide fluid storage and permeability while under negative pressure may require the fluid removal assembly 148 to have a higher volume of fluid capacity compared to the instillation matrix 152 that may be under positive pressure. Fluid being instilled or delivered to the tissue site 112 through the separate instillation matrix 152 may not be required to pass through portions of the treatment device 101, such as the fluid removal assembly 148, which may be higher volume. Such a configuration may enhance the distribution and efficient use of the instillation fluid.

Continuing generally with FIGS. 1-6B, further described is a method for providing fluid instillation and negative-pressure treatment at a tissue site. In some embodiments, a method for providing fluid instillation and negative-pressure treatment at a tissue site may include positioning the treatment device 101 adjacent to the tissue site 112. The treatment device 101 may include the instillation matrix 152 and the fluid removal assembly 148 separate from the instillation matrix 152. As previously discussed, in some embodiments, the tissue site 112 may be the abdominal cavity 111, and positioning the treatment device 101 adjacent to the tissue site 112 may include placing at least a portion of the treatment device 101 proximate a paracolic gutter in the abdominal cavity 111, such as the first paracolic gutter 115 and/or the second paracolic gutter 117. Further, in some embodiments, the method may include covering the treatment device 101 with the sealing member 128 to provide a sealed space between the sealing member 128 and the tissue site 112. In some embodiments, the method may include sizing the treatment device 101 for placement at the tissue site 112. As previously mentioned, sizing the treatment device 101 may include cutting or tearing the treatment device 101. In some instances, the treatment device 101 may include visual indicia for guiding a user to customize the treatment device to a desired size.

The method may further include coupling the fluid source 108 in fluid communication with the instillation matrix 152, and coupling the negative-pressure source 106 in fluid communication with the fluid removal assembly 148. The method may further include supplying instillation fluid from the fluid source 108 to the tissue site 112 through the instillation matrix 152. Additionally, the method may include providing negative pressure from the negative-pressure source 106 to the tissue site 112 through the fluid removal assembly 148, and extracting fluid from the tissue site 112 through the fluid removal assembly 148. Following completion of negative-pressure and/or fluid instillation therapy, a user may remove the treatment device 101 as a largely intact structure, thus maintaining an ease of use of the treatment device 101.

Referring now to FIG. 7A, another example embodiment of a treatment device 201 for use in the therapy system 100 is shown. In this embodiment, treatment device 201 may include substantially similar components to the treatment device 101 of FIG. 3, however may differ in the arrangement and functionality of the individual features. For example, treatment device 201 may include a plurality of fluid removal pathways 150, which may be positioned between multiple liquid-impermeable layers of the dressing 202 and fluidly connected to the fluid removal hub 154. However, in this example embodiment, the treatment device 201 may include an instillation matrix 252 having a plurality of fluid delivery tubes 258 that may be attached to the distribution hub 260, and the fluid delivery tubes 258 may hang loosely below the dressing 202. In this embodiment of the treatment device 201, a user may be able to individually position each of the fluid delivery tubes 258 within an abdominal cavity of a patient. Thus, a user may choose to either evenly spread the fluid delivery tubes 258 throughout the abdominal cavity to provide a full, uniform rinse of the abdomen, or alternatively, the user may choose to focus the fluid delivery tubes 258 to any areas of particular concern in order to provide a more thorough wash. The treatment device 201 may allow the user to determine this on a case-by-case basis. In some embodiments, the plurality of fluid delivery tubes 258 may comprise polyurethane film or foam bags with perforations. For example, the fluid delivery tubes 258 may be constructed using two layers of polyurethane film of approximately 100 micrometers in thickness that are edge-welded together. The fluid delivery tubes 258 may have open ends for targeted fluid delivery. Similarly, in such embodiments, the distribution hub 260 may be constructed of two layers of approximately 100 micrometer thickness polyurethane film welded together. In some embodiments, within each of the fluid delivery tubes 258 and distribution hub 260 may be a central core adapted to ensure that an open pathway is maintained and to aid a user with handling during placement. For example, this central core may be open-cell reticulated polyurethane foam. Dimensions of the central core material positioned within the fluid delivery tubes 258 may vary, for example the central core material may range from around 2 mm to 10 mm in thickness by about 5 mm to 15 mm in width. In some embodiments, the central core material may be around 6 mm in thickness by 10 mm in width. The length of the central core material may be varied based on overall sizing considerations of the treatment device 201. Some embodiments of the treatment device 201 may include a central core material having a width that varies along its length, which may allow for break points to provide user customization and sizing. In some instances, the fluid delivery tubes 258 may be adapted so that any instillation fluid remaining within the fluid delivery tubes 258 following delivery of instillation fluid by the fluid source 108 may be squeezed from the fluid delivery tubes 258 when negative pressure is applied to the treatment device 201, thus ensuring that substantially all instillation fluid is emptied from the fluid delivery tubes 258 to better regulate the volume of instillation fluid provided during therapy cycles.

Figure 7B:
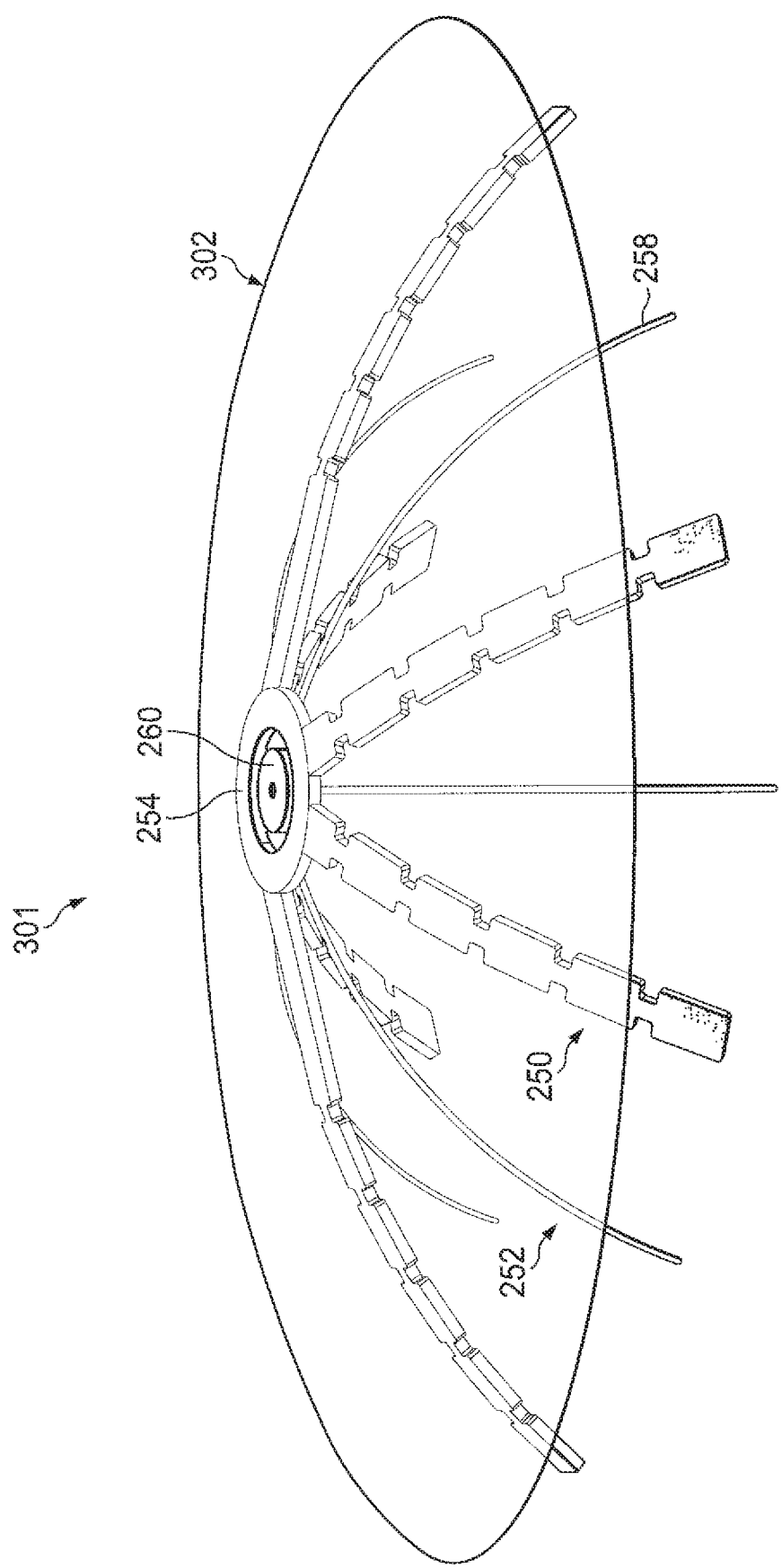

FIG. 7B shows a similar embodiment of a treatment device 301 to that of FIG. 7A, however rather than including a plurality of fluid removal pathways that are positioned between liquid-impermeable layers of the dressing 202, the treatment device 301 includes both fluid removal pathways as well as fluid instillation pathways that may be individually positioned. In some embodiments, a treatment device 301 may include a dressing 302 having fluid removal pathways 250 that are attached to the fluid removal hub 254 and extend freely below the liquid-impermeable layers of the dressing 302. Additionally, in some embodiments, the treatment device 301 may also include an instillation matrix 252 having fluid delivery tubes 258 which may also extend freely from the underside of the dressing 302. Thus, in such embodiments, a user may choose to focus the fluid removal pathways 250 as well as the fluid delivery tubes 258 to any areas of concern within the abdominal cavity of a patient. The user may also choose to spread the fluid removal pathways 250 and fluid delivery tubes 258 evenly within the patient's abdomen to provide a full rinse of the abdominal cavity. In such embodiments, the dressing 302 may be supplied with the fluid removal pathways 250 and fluid delivery tubes 258 attached to liquid-impermeable layers of the dressing 302, or separately for user assembly.

Figure 7C:
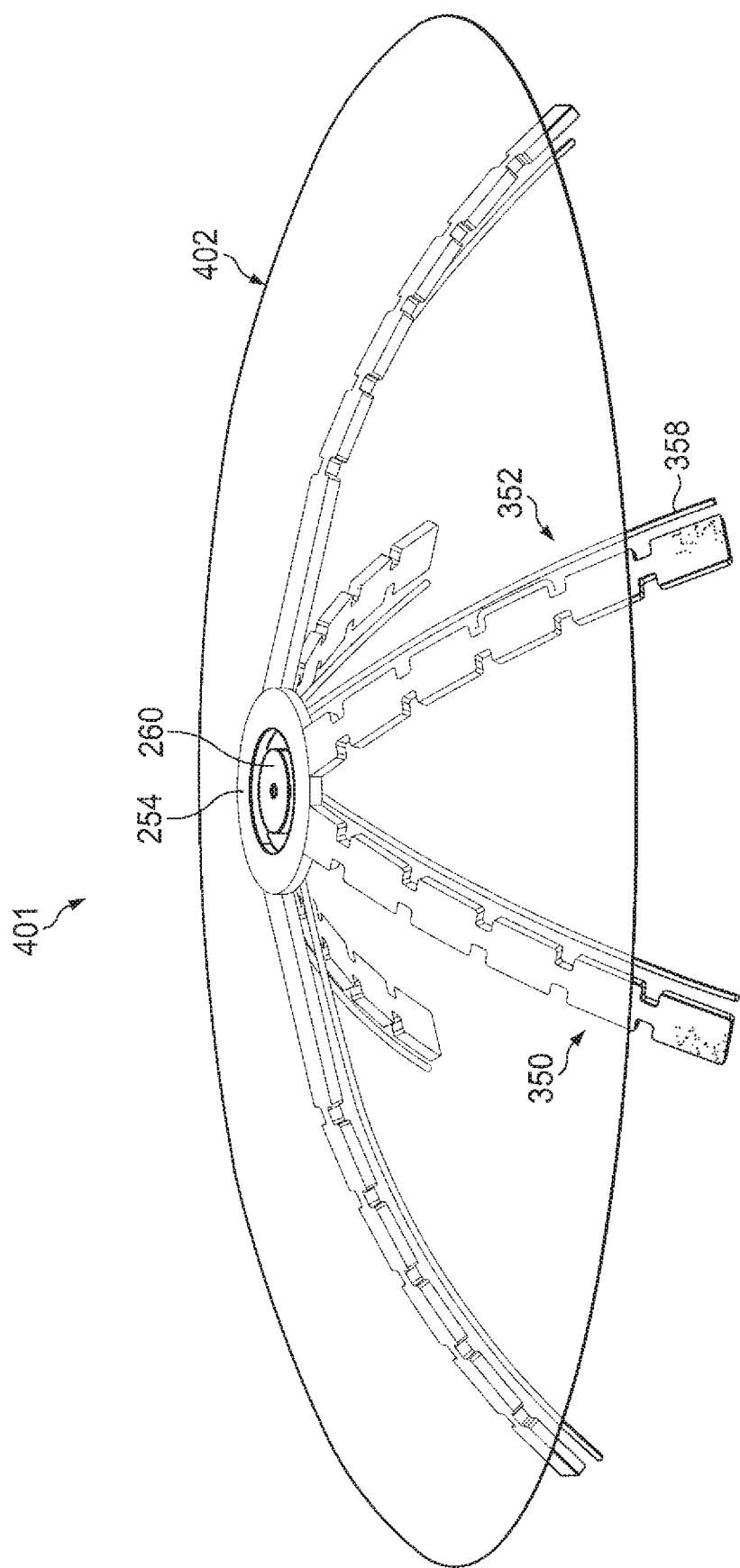

FIG. 7C also shows another embodiment of a treatment device 401, which similarly to the treatment device 301 of FIG. 7B, may include both a plurality of fluid removal pathways 350 and instillation matrix 352 having fluid delivery tubes 358 which extend loosely adjacent or below the liquid-impermeable layers of the dressing 402. However, in some embodiments, as shown in FIG. 7C, each of the fluid removal pathways 350 may be paired with a fluid delivery tube 358 for positioning in the same area within a patient's abdominal cavity. In such embodiments, the fluid removal pathways 350 may be paired with the fluid delivery tubes 358, however two separate fluid pathways would still be maintained. Such an arrangement may offer the benefit that the fluid that is instilled to a location within an abdominal cavity may be subsequently removed from the same area, which may be important in cases where regions of the abdominal cavity are highly contaminated, to avoid cross-contamination with other areas of the abdominal cavity. Since neither the fluid removal pathways 350 nor the fluid delivery tubes 358 are positioned within liquid-impermeable layers of the dressing 402, the treatment device 401 may therefore require a separate dressing 402 comprising liquid-impermeable layers, which may be applied to the patient's abdominal cavity after the combined fluid removal pathways 350 and fluid delivery tubes 358 have been positioned. Depending on specific manufacturing and user requirements, the dressing 402 may be supplied attached to the fluid removal pathways 350 and instillation matrix 352 or separate for user assembly.

Figure 8:
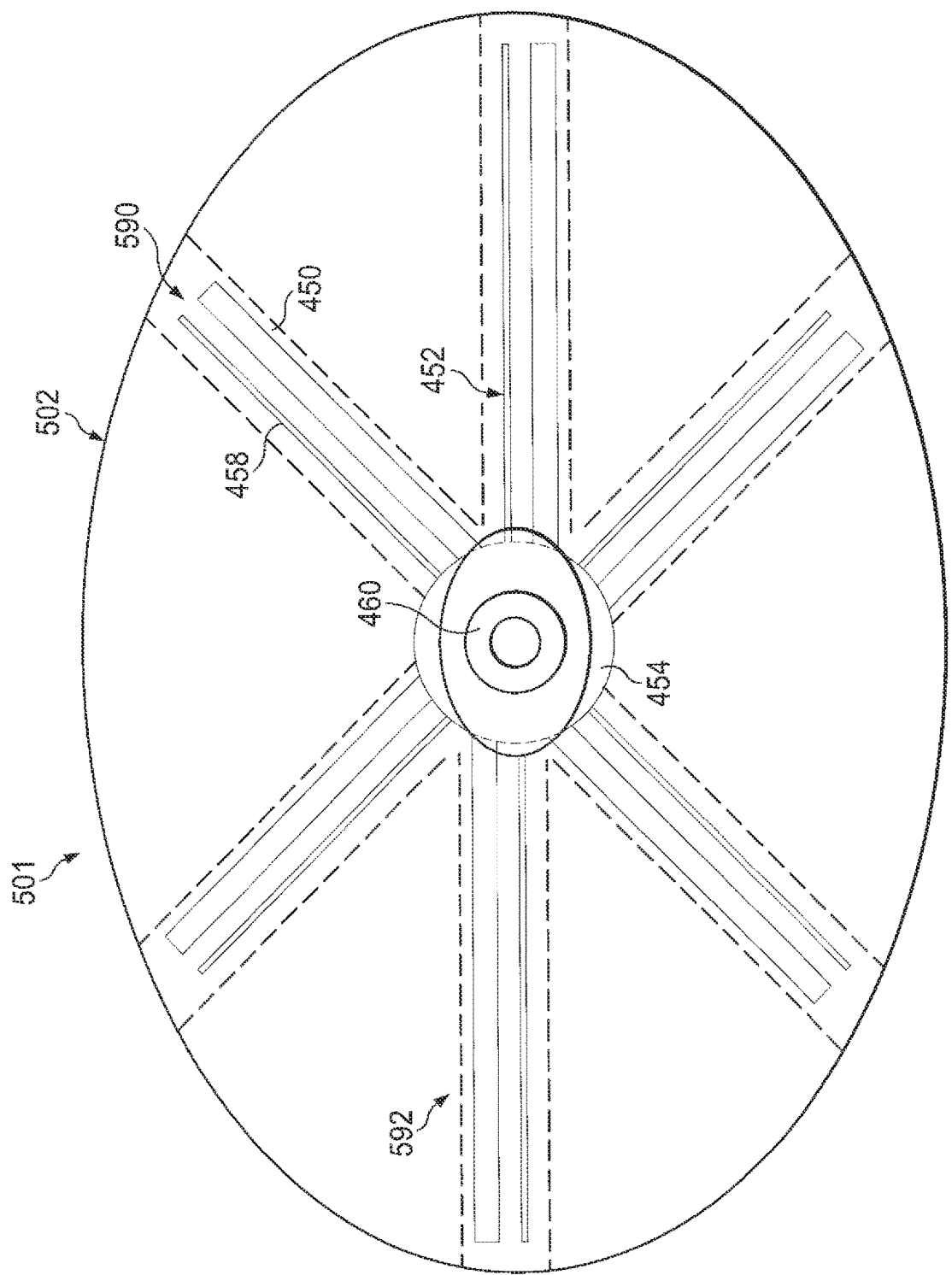
FIG. 8 is a schematic, plan view of another illustrative abdominal treatment device that may be associated with the therapy system of FIG. 1.

Referring now to FIG. 8, another example illustrative embodiment of a treatment device 501 is shown. In this embodiment, the fluid removal pathways 450 and the fluid delivery tubes 458 of the instillation matrix 452 are formed as part of the dressing 502, with each fluid removal pathway 450 running adjacent and parallel to a fluid delivery tube 458, thus forming parallel pathways 590. In some embodiments, the parallel pathways 590, each of which may include a fluid removal pathway 450 and a fluid delivery tube 458, may be connected between segments of liquid-impermeable layers of the dressing 502 by a perforated joint, such as perforations 592, in the liquid-impermeable layers of the dressing 502. Thus, each parallel pathway 590 may be individually moveable by cutting or tearing along its surrounding perforations 592 and placed within a specific area of the abdominal cavity, such as adjacent to small bowel loops, paracolic gutters, retroperitoneal space, lymphatic system, etc. Additionally, some embodiments of the dressing 502 may also include an additional perforated joint, or line of perforations, between each of the fluid removal pathways 450 and fluid delivery tubes 458 within the parallel pathways 590. Thus, each of the fluid removal pathways 450 may also be separately moveable from the corresponding paired fluid delivery tube 458, and positioned as desired within the abdominal cavity. Regardless of position, each of the fluid removal pathways 450 may remain fluidly connected to fluid removal hub 454, and each of the fluid delivery tubes 458 may remain fluidly connected to the distribution hub 460.

Figure 9:
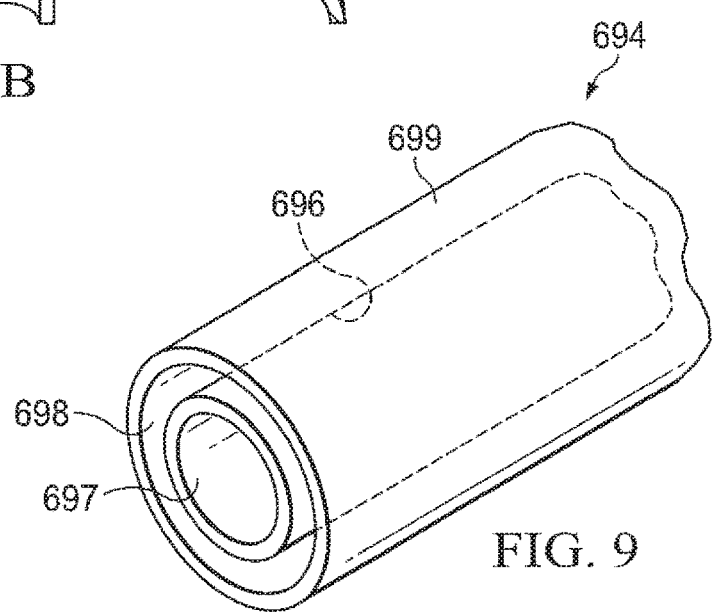
FIG. 9 is a schematic diagram illustrating additional details of a fluid conduit that may be associated with a portion of an abdominal treatment device of the therapy system of FIG. 1.

FIG. 9 illustrates features of some example embodiments of a treatment device where fluid removal pathways and fluid instillation pathways may be combined into single pathways. For example, a single fluid removal pathway and a single fluid instillation pathway may be combined into a single tube-like structure, such as combination tube 694. The combination tube 694 may include a central bore 696, which may be formed by an inner lining 697, which may be a film, such as a polyurethane film. The combination tube 694 may also include an outer lumen 698, which may be formed by an outer lining 699, which may also be a film, such as a polyurethane film. Either the central bore 696 or the outer lumen 698 may be used for either the fluid removal pathway or the fluid instillation pathway, depending on the specific embodiment.

Figure 10C:
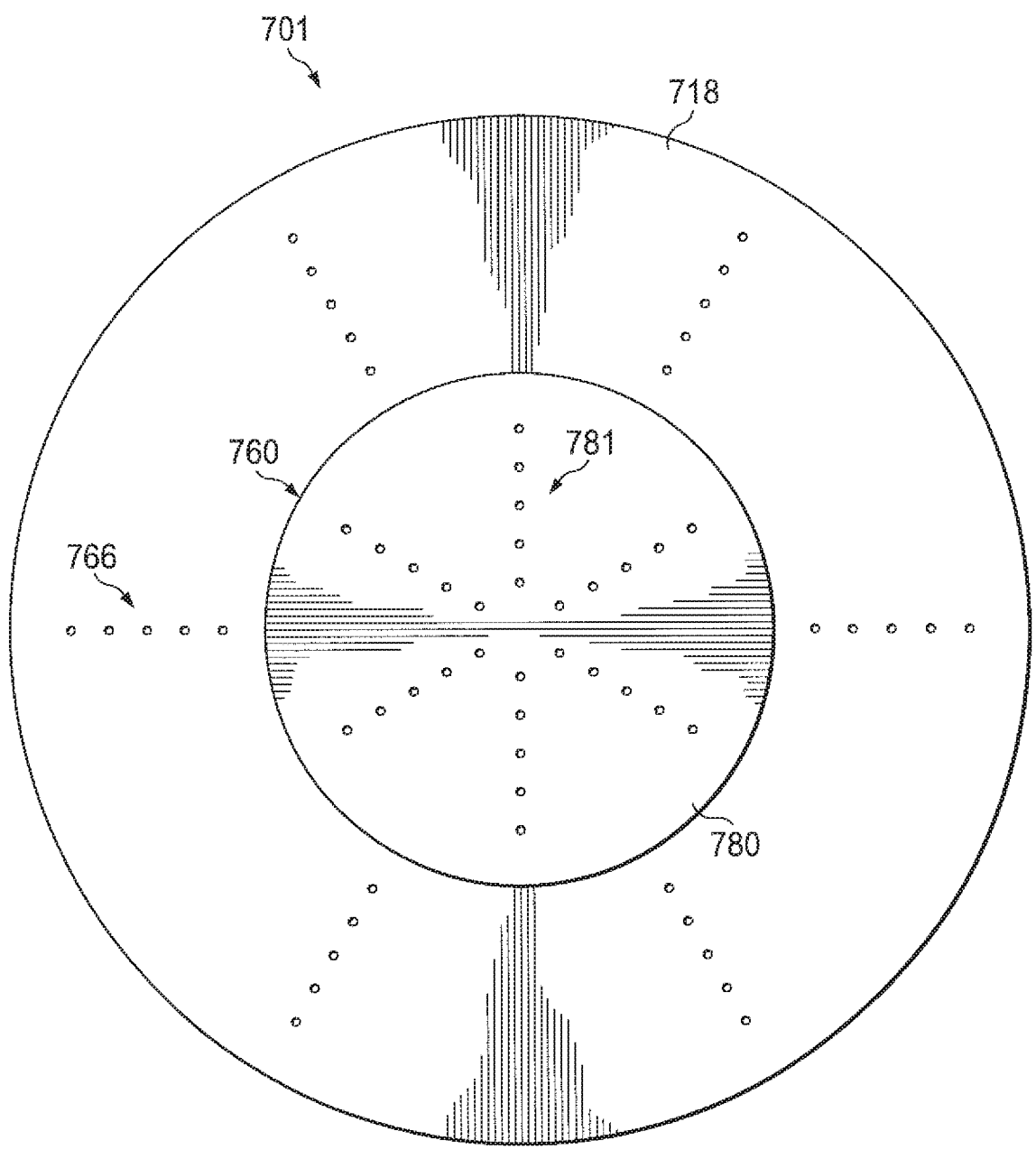

Referring now to FIGS. 10A-10C, an illustration of another example embodiment of a treatment device 701 for use with the therapy system 100 is shown. In some embodiments, the treatment device 701 may include a dressing 702, which may be formed of multiple liquid-impermeable layers, or visceral protective layers, such as first liquid-impermeable layer 718 and second liquid-impermeable layer 720. The treatment device 701 may also include a delivery connector 763 for delivering instillation fluid to the treatment device 701. The treatment device may also include a fluid removal hub 754 for communicating negative pressure to portions of the treatment device 701 and for removing fluid from the treatment device 701 and abdominal cavity. As depicted in FIG. 10A, the treatment device 701 may further include a fluid delivery vessel 760 for distributing instillation fluid. The fluid delivery vessel 760 may be a flexible vessel that is fluidly connected to an instillation source, such as fluid source 108 of therapy system 100. In some embodiments, the body of the fluid delivery vessel 760 may be constructed from one or more portions of a film material having a thickness ranging from 25 micrometers to 500 micrometers. For example, the fluid delivery vessel 760 may be constructed from a polyurethane film with a thickness ranging from 50 micrometers to 200 micrometers. In some instances the fluid delivery vessel 760 may be of a perimeter-welded construction having a pre-determined volume. Some embodiments of the fluid delivery vessel 760 may include internal welds between portions of the polyurethane film forming the body of the fluid delivery vessel 760 to reduce swelling of the vessel when under pressure. Internal welds may also be incorporated for reducing the internal volume of the fluid delivery vessel 760 or to help direct instillation fluid within the fluid delivery vessel 760 to help ensure even distribution out of the fluid delivery vessel 760 and into an abdominal cavity.

As shown in FIGS. 10A-10C, the fluid delivery vessel 760 may be integrated with the dressing 702 as part of the treatment device 701. In some instances, the dressing 702 and the fluid delivery vessel 760 essentially may form a two-chamber structure, with the two chambers placed in a vertical stack. As depicted in FIGS. 10A-10C, the fluid delivery vessel 760 may be formed from a vessel layer 780 which is adhered or welded to an underside of the dressing 702, such as to the first liquid-impermeable layer 718. In some embodiments, the fluid delivery vessel 760 may be fluidly coupled to the delivery connector 763, and thus a source of instillation fluid, through the dressing 702 via a sealed, welded opening, such as dressing opening 779, which may pass through the visceral protective layers, first liquid-impermeable layer 718 and second liquid-impermeable layer 720, of the dressing 702.

The vessel layer 780 may include perforations, fenestrations, or openings, such as vessel apertures 781 to allow for transfer of instillation fluid out of the fluid delivery vessel 760. The vessel apertures 781 may be sized to provide a back pressure while the fluid delivery vessel 760 is filled by ensuring that the flow rate out of the fluid delivery vessel 760 is less than the filling flow rate. For example, the vessel apertures 781 may have a diameter within the range of 0.2 mm to 1.0 mm. The vessel apertures 781 may also have a diameter that is outside of this range, depending on the number and/or pattern of vessel apertures 781 in the vessel layer 780. As depicted in FIG. 10A, the volume or size of the fluid delivery vessel 760 may expand or swell during an instillation, or fluid delivery, phase of treatment.

During operation, the instillation fluid may enter the fluid delivery vessel 760, and as the fluid delivery vessel 760 becomes filled, a back pressure may be created, which thus pressurizes the fluid delivery vessel 760 before instillation fluid may actually be released out from the fluid delivery vessel 760. This functionality may help ensure that fluid may be more evenly dispersed through the vessel apertures 781 and thus provide an even distribution of instillation fluid from the entire area of the fluid delivery vessel 760. However, it is important to note that the fluid delivery vessel 760 may be designed so that the level of back pressure created by the fluid delivery vessel 760 remains less than a threshold pressure for triggering an alarm on fluid instillation systems, such as the fluid source 108 of therapy system 100. Furthermore, the vessel apertures 781 may be arranged in a way to provide a higher flow rate in certain locations of the fluid delivery vessel 760 and a lower flow rate in others, such as by including an asymmetrical pattern of vessel apertures 781. Thus, the pattern of vessel apertures 781 may dictate fluid distribution, and different versions of fluid delivery vessels 760 may be produced which are designed to target certain areas or organs of an abdominal cavity or other tissue sites. Additionally, in some embodiments, the vessel layer 780 of the fluid delivery vessel 760 may incorporate welds or other methods to produce a quilting effect within the fluid delivery vessel 760 to reduce the internal volume of the fluid delivery vessel 760, to eliminate swelling due to back pressure, or to aid in fluid distribution. This feature may thus assist with reducing patient discomfort and associated risks.

The possible delay in releasing instillation fluid from the fluid delivery vessel 760 into an abdominal cavity or other tissue site may provide the benefit of allowing the temperature of the instillation fluid to balance with the body's core temperature to reduce risks of thermal shock. Once released from the fluid delivery vessel 760, the instillation fluid may flow through the abdominal cavity and into the paracolic gutters, cleansing throughout its path. Additionally, a dwell time for instillation fluid may occur, as some instillation fluid may remain in the fluid delivery vessel 760 following an instillation cycle. As negative pressure is applied to the treatment device 701, the instillation fluid may be removed through the fluid removal pathways 750 (shown in FIG. 10B), continuing to wash abdominal contents as it is removed from the abdominal cavity. In some instances, instillation fluid remaining in the fluid delivery vessel 760, as mentioned above, may be removed during the application of negative pressure, acting as a bolus of clean rinsing fluid as it is removed. For example, after the majority of the instillation fluid is removed from the abdominal cavity and a negative pressure begins to build up within the cavity, the components of the treatment device 701 may be drawn downwards and the remaining fluid in the fluid delivery vessel 760 may be removed as a rapidly-moving bolus of fluid, thus acting as a final and secondary rinse. Fluid instillation and negative-pressure cycles may be repeated as necessary or desired.

Referring now primarily to FIG. 10B, similar to other embodiments previously described in detail, the treatment device 701 may include a plurality of fluid removal pathways 750, each of which may be fluidly coupled to the fluid removal hub 754. Thus, the fluid removal hub 754 may serve as a distribution mechanism for communicating negative pressure to each of the fluid removal pathways 750. Each of the fluid removal pathways 750 may include a manifold member, for communicating negative pressure and drawing fluids through the fluid removal pathways 750. For example, the manifold member may be constructed from an open-cell foam or non-woven fabric, such as GRANUFOAM™. The fluid removal pathways 750 may be incorporated within the dressing 702, and thus between the visceral protective layers, first liquid-impermeable layer 718 and second liquid-impermeable layer 720. Incorporating the fluid removal pathways 750 between the visceral protective layers may help protect the abdominal cavity from the manifold member, which may otherwise present risks of granulation. In some embodiments, the fluid removal pathways 750 may be formed by welding together portions of the first liquid-impermeable layer 718 and the second liquid-impermeable layer 720, to form fluid channels between the film layers. Referring now primarily to FIG. 10C, the first liquid-impermeable layer 718, and also perhaps the second liquid-impermeable layer 720, may include fenestrations, such as apertures 766, which may be positioned along each of the fluid removal pathways 750. Fluid may be drawn into the fluid removal pathways 750 through the apertures 766 in the first liquid-impermeable layer 718 on the underside of each of the fluid removal pathways 750. Each of the fluid removal pathways 750 may also include openings at its end, which may allow for a large degree of fluid removal from the paracolic gutters of a patient. Providing focused fluid removal in the low points of a patient's abdomen, such as the paracolic gutters, may help ensure that the abdomen is fully washed during the instillation and removal therapy cycles.

Figure 11B:
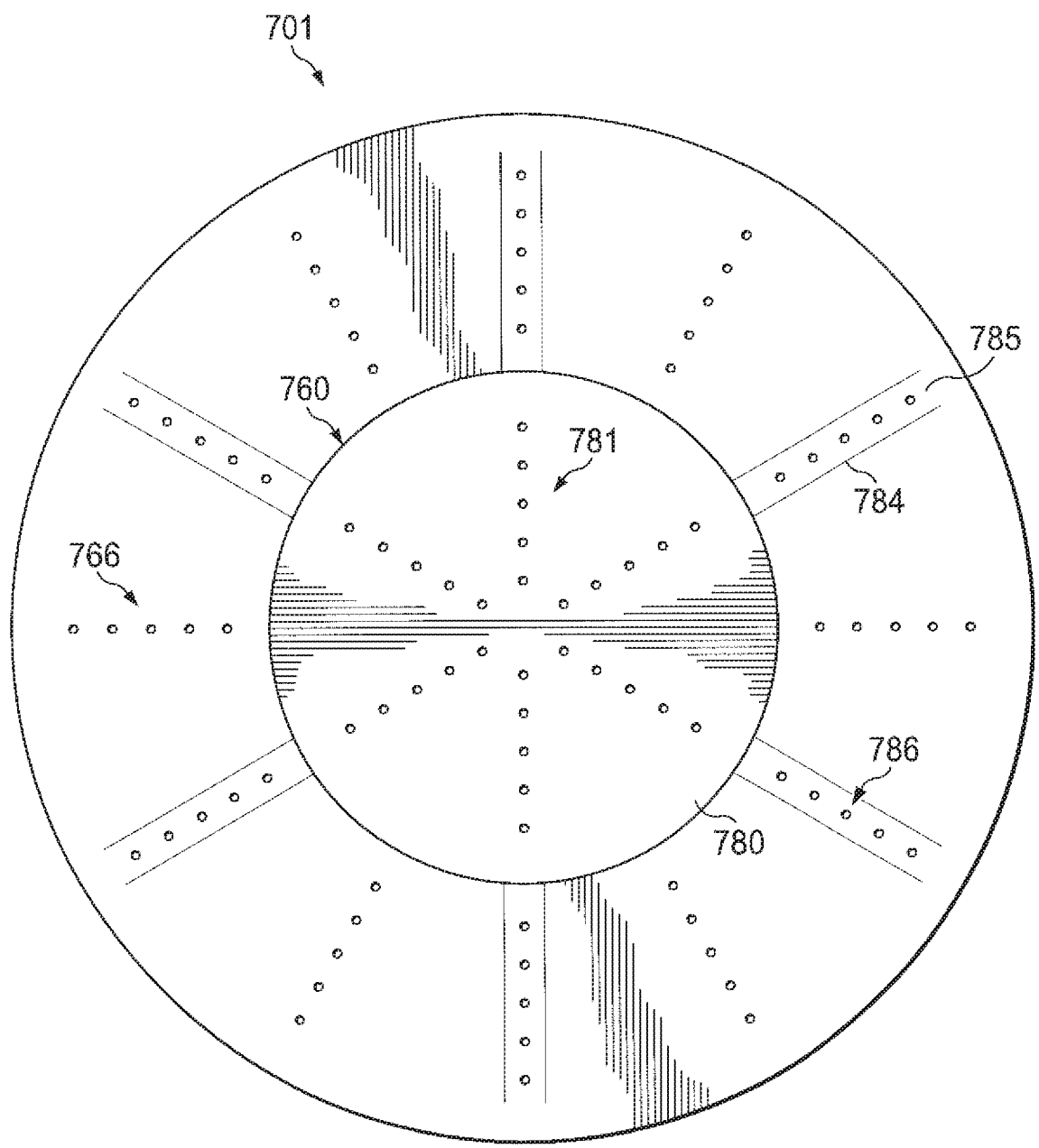

FIGS. 11A-11B show another example embodiment of treatment device 701, which in many respects may be similar to the embodiment of the treatment device 701 discussed with respect to FIGS. 10A-10C. However, in the illustrative embodiment shown in FIGS. 11A-11B, the treatment device 701 may incorporate a fluid delivery vessel 760 which includes a vessel chamber 782 as well as radial channels 784 which may be for extending down the inside of an abdominal wall and into the paracolic gutters of a patient's abdomen. This embodiment may particularly allow for even distribution of instillation fluid into an abdominal cavity, while simultaneously providing targeted washing of the paracolic gutters with clean instillation fluid. The radial channels 784 may have open ends 785 as well as channel apertures 786 along the length of each of the radial channels 784. In some embodiments, the radial channels 784 may be designed so as to limit flow into the paracolic gutters. The open-ended design of the radial channels 784 may also allow for the radial channels 784 to be cut and sized to suit the needs and proportions of individual patients.

Figure 12A:
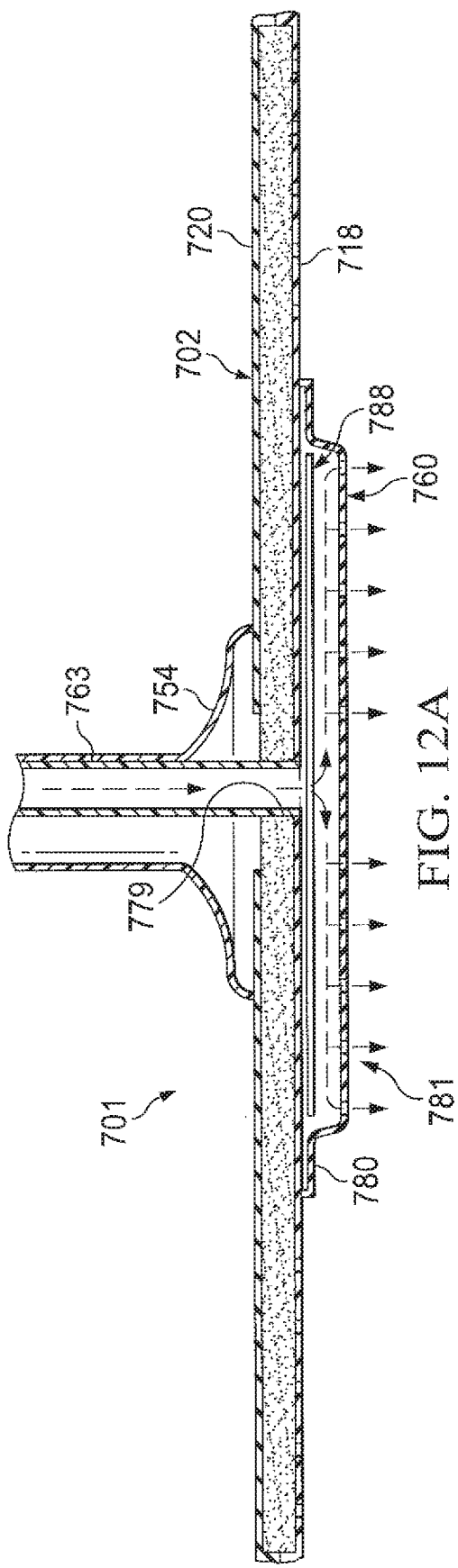
FIGS. 12A-12B are schematic diagrams, with portions in cross-section, of another illustrative embodiment of an abdominal treatment device that may be associated with the therapy system of FIG. 1.
Figure 12B:
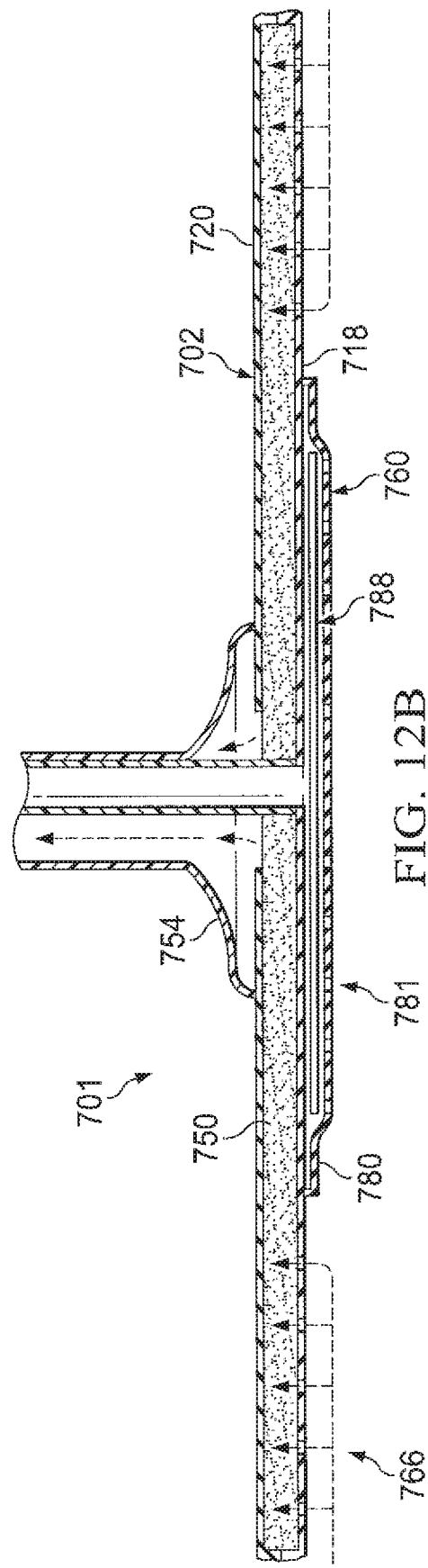

Referring now to FIGS. 12A-12B, another illustrative embodiment of the treatment device 701 is shown. Once again, many of the features of treatment device 701 of FIGS. 12A-12B may be the same or similar to those of the embodiments of the treatment device 701 discussed with respect to FIGS. 10-11. In the example embodiment of FIGS. 12A-12B, the fluid delivery vessel 760 may incorporate an internal manifold or matrix, such as internal manifold matrix 788, to help ensure that the fluid instillation pathway from the delivery connector 763, through the fluid delivery vessel 760, and out of vessel apertures 781 remains open and not occluded or sealed when subjected to negative pressure. Example materials for internal manifold matrix 788 may include foams, such as polyurethane foam, Libeltex TDL2, embossed films, or some other formed structure.

FIGS. 13A-13B show another example embodiment of a treatment device 801 for use with the therapy system 100, which in many respects may be similar to the embodiments of treatment devices previously discussed. In some embodiments, the treatment device 801 may include a dressing 702 and a fluid delivery vessel, such as fluid delivery vessel 860, which may be a separate component that may be supplied unattached to the liquid-impermeable layers of the dressing 702, for user assembly during application. For example, in some embodiments, the fluid delivery vessel 860 may be formed by two layers, such as a lower, vessel layer 880 and an upper vessel layer 883. In some embodiments, the fluid delivery vessel 860 may be in the form of a bag or an encapsulated foam. The vessel layer 880 may include openings, such as vessel apertures 881 on the lower surface, or underside, of the fluid delivery vessel 860 for delivering fluid out of the fluid delivery vessel 860 and into an abdominal cavity of a patient. In some embodiments, the fluid delivery vessel 860 may be fluidly connected to an instillation source, such as fluid source 108, through an opening in the upper vessel layer 883, which may physically and fluidly connect to an end portion of delivery connector 763. Similar to other embodiments previously described, the fluid delivery vessel 860 may swell during the fluid instillation cycle of therapy, as fluid is delivered to and may fill the fluid delivery vessel 860 under pressure.

Importantly, by allowing the fluid delivery vessel 860 to be supplied separately from the other portions, such as dressing 702, of the treatment device 801, a surgeon or other caregiver may be able to better determine the requirement of fluid instillation in the abdomen of a patient and apply an appropriately sized or configured fluid delivery vessel on a case-by-case basis. It is also possible for some embodiments of fluid delivery vessels, such as fluid delivery vessel 860, to be supplied as an accessory to current abdominal dressings, such as the ABThera® dressings, commercially available from Kinetic Concepts, Inc., of San Antonio, Tex.

FIGS. 14A-14B refer to an example embodiment of a treatment device 801 that may be similar to the illustrative embodiment of a treatment device 801 shown in FIGS. 13A-13B. However, in the example embodiment of FIGS. 14A-14B, the fluid delivery vessel 860 may incorporate an additional component which may be a collapsing or non-collapsing matrix, such as manifold matrix 884, which may allow the fluid delivery vessel 860 to fill with instillation fluid. In some embodiments, the fluid delivery vessel 860 may include a lower layer, vessel layer 880, which may be occlusive, and an upper layer, such as upper vessel layer 883, which may incorporate perforations, fenestrations, or openings, such as vessel upper apertures 885. The vessel upper apertures 885 may allow for the flow of instillation fluid out of an upper surface of the fluid delivery vessel 860, which may occur after the fluid delivery vessel 860 has been filled with an instillation fluid during a therapy cycle. In some instances, by ensuring that the fluid delivery vessel 860 is fully filled with instillation fluid before fluid migrates out into the abdominal cavity, the need to create a back pressure within the fluid delivery vessel 860 for ensuring even fluid distribution may be eliminated.

Figure 15:
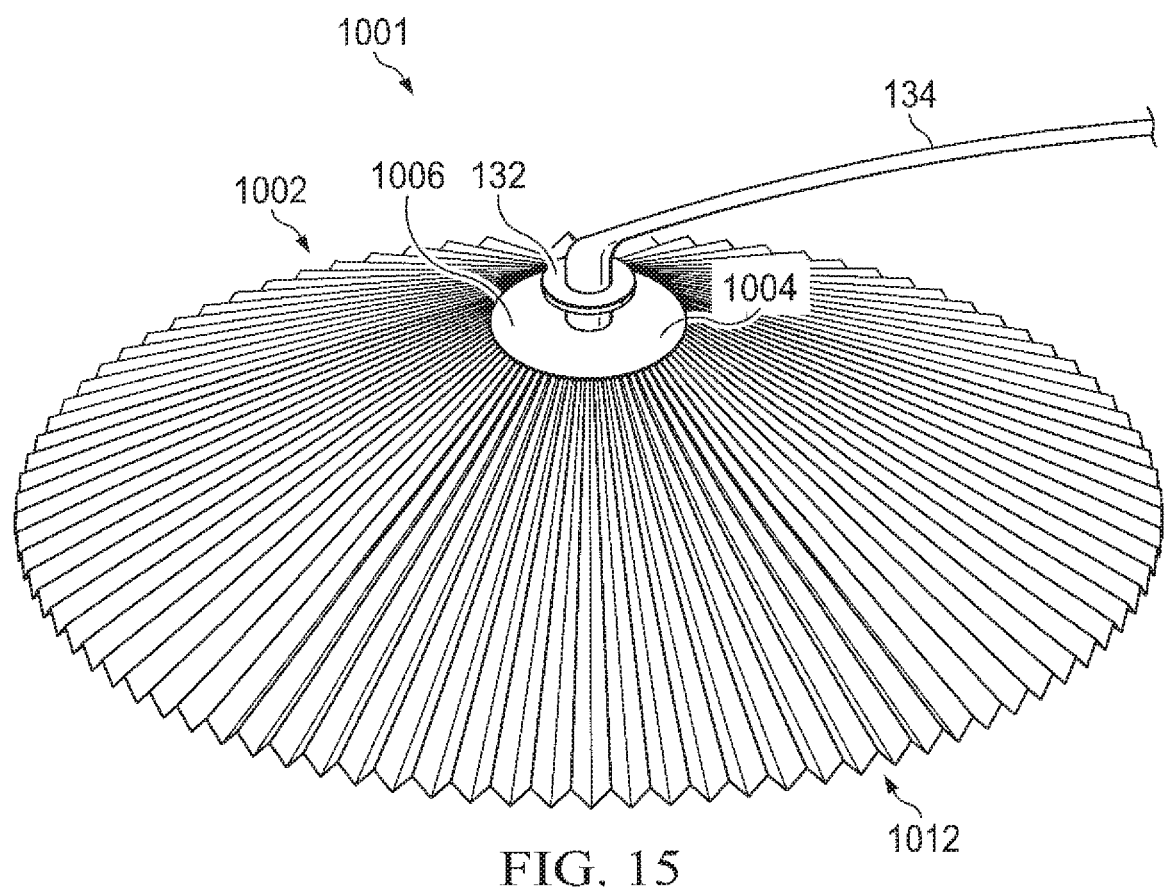
FIG. 15 is a schematic, plan view of another illustrative embodiment of an abdominal treatment device that may be associated with some embodiments of the therapy system of FIG. 1.

Referring now to FIG. 15, an illustration of another example embodiment of a treatment device 1001 for use with the therapy system 100 is shown. In one embodiment the treatment device 1001 may include a single layer, such as occlusive layer 1002, for dividing the abdominal cavity into two, vertically-stacked chambers or compartments. The treatment device 1001 may also include a fluid removal manifold 1004, which may be positioned within a central portion of the occlusive layer 1002, and may fluidly communicate negative pressure to channels of the occlusive layer 1002 for collecting and removing fluid from the abdominal cavity. Additionally, the treatment device 1001 may include a pressurized distribution vessel 1006, which may distribute instillation fluid across the occlusive layer 1002 to regions of the abdominal cavity. As previously discussed with respect to other embodiments, a conduit 134 for transporting negative pressure and/or instillation fluid may be fluidly connected to the treatment device 1001 at an interface 132.

In operation, instillation fluid may be delivered by a suitable fluid source, as previously discussed with respect to other embodiments, and when delivered to the pressurized distribution vessel 1006 of the treatment device 1001, the instillation fluid may be forced across the surface of the occlusive layer 1002. The installation fluid may flow through formed pathways over the occlusive layer 1002 until it reaches the furthest extent of the occlusive layer 1002 and comes into contact with the abdominal contents, and eventually the paracolic gutters. As the instillation fluid flows across the top surface of the occlusive layer 1002, it may be warmed to body temperature due to body heat and being spread over a large area. As previously described, a dwell time of the instillation fluid may occur, with some of the instillation fluid remaining in the pressurized distribution vessel 1006 on the instillation surface of the occlusive layer 1002, which may later act as a bolus of clean fluid when removed.

During the negative-pressure, or fluid removal cycle, the instillation fluid may be withdrawn from the abdominal cavity by being drawn along formed pathways on the underside, or bottom surface, of the occlusive layer 1002. As negative pressure is applied, the occlusive layer 1002 may be drawn downwards and tightly compressed against the abdominal contents. This movement allows the abdominal contents, such as internal organs, to be in contact with the instillation fluid as it is drawn along the formed pathways on the underside of the occlusive layer 1002. During negative-pressure application, the remaining fluid in the pressurized distribution vessel 1006 may be removed as a rapidly-moving bolus of fluid, thus acting as a final rinse, as previously discussed with respect to other embodiments.

Referring now also to FIG. 16, a schematic cross-section view of portions of the treatment device 1001 and conduit 134 of FIG. 15 is shown. In this illustrative figure, it can be seen how the occlusive layer 1002 may divide an abdominal cavity into two different chambers or compartments. For example, below the occlusive layer 1002 may be a fluid removal chamber 1008, which sits against the internal organs, and above the occlusive layer 1002 may be a fluid instillation chamber 1010, which may be in close proximity with the skin of the patient. By splitting the abdominal cavity in such a manner, the occlusive layer 1002 may ensure that instilled fluids may reach the furthest extent of the treatment device 1001 within the abdomen before being removed. Importantly, the occlusive layer 1002 may also act as a visceral protective barrier. In some embodiments, the occlusive layer 1002 may be biased to collapse downward and to substantially form a seal under the application of negative pressure, which may help minimize cross-contamination between the fluid instillation chamber 1010 and the fluid removal chamber 1008.

Referring again to both FIGS. 15 and 16, in some embodiments, the occlusive layer 1002 may be formed from a single piece or sheet of film, such as a polyurethane film. In some embodiments, the occlusive layer 1002 may provide fluid pathways both below the occlusive layer 1002 in the fluid removal chamber 1008 and above the occlusive layer 1002 in the fluid instillation chamber 1010. For example, the fluid pathways may be formed by pleats 1012 in the occlusive layer 1002, which may be created using high-frequency welding techniques. For example, high-frequency (HF) or radio-frequency (RF) welding may involve joining portions of the occlusive layer 1002 together using high frequency electromagnetic energy to fuse the material of the portions of the occlusive layer 1002. The pleats 1012 may be arranged such that they evenly distribute the fluid to the distal edge of the occlusive layer 1002. The number of pleats 1012 may be varied to further control the flow of instillation fluid into the abdominal cavity as necessary or desired.

In some embodiments, the fluid removal manifold 1004 may be a flexible vessel pneumatically or fluidly connected to the container 110 and negative-pressure source 106 through a removal pathway of conduit 134. The fluid removal manifold 1004 may be made from multiple films welded together, which may be polyurethane films welded together around a perimeter. For example, the fluid removal manifold 1004 may include an upper manifold film 1014 and a lower manifold film 1016. As shown in FIG. 16, in some embodiments, the fluid removal manifold 1004 may include openings or fenestrations, which may be included as inlets 1018 as part of the lower manifold film 1016. These inlets 1018 on the underside of the fluid removal manifold 1004 may be for distributing negative pressure to the fluid removal chamber 1008 and recruiting fluids from the fluid removal chamber 1008. The inlets 1018 may be sized according to particular suction needs. In some embodiments, the fluid removal manifold 1004 may include a manifold material 1019, which may be contained within the upper manifold film 1014 and the lower manifold film 1016. The manifold material 1019 may include a variety of different materials suitable for communicating or transporting fluid. For example, in some embodiments, the manifold material 1019 may include an open-cell foam having a pores of approximately 6 mm in diameter.

In some embodiments, the pressurized distribution vessel 1006 may be a flexible vessel that is in fluid communication with the fluid source 108, through an instillation pathway of conduit 134. The volume of the pressurized distribution vessel 1006 may vary, and in some embodiments, may be reduced using internal welds which, may in turn, assist with building localized pressure for improved distribution of the instillation fluid. Suitable materials for forming the structure of the pressurized distribution vessel 1006 may include sheets of film, such as polyurethane films, which may be welded together around a perimeter. For example, the pressurized distribution vessel 1006 may include an upper vessel film 1020 and a lower vessel film 1022. As shown in FIG. 16, in some embodiments, the pressurized distribution vessel 1006 may include outlets 1024 on its undersize, as part of the lower vessel film 1022, for allowing the installation fluid to exit the pressurized distribution vessel 1006 when a particular internal pressure within the pressurized distribution vessel 1006 is reached. For example, the outlets 1024 may be sufficiently small to create a back-flow for helping to drive even distribution of the instillation fluid out of the pressurized distribution vessel 1006, but not so small such that the outlets 1024 would cause a potential blockage alarm in the therapy system 100. In some embodiments, the outlets 1024 may have a diameter between about 0.2 mm and 1 mm. The outlets 1024 may be in the form of perforations or fenestrations. The outlets 1024 may also be arranged in one or more patterns to help dictate distribution, and different versions of the pressurized distribution vessel 1006 with different arrangements of outlets 1024 may be produced that are designed for targeting certain areas or organs. For example, in some embodiments, the outlets 1024 may be arranged in an evenly-spaced pattern around the perimeter of the pressurized distribution vessel 1006.

FIG. 17 shows a schematic cross-section view of portions of another illustrative embodiment of a treatment device 2001 and conduit 134. In this illustrative figure, it can be seen how the occlusive layer 2002 may include multiple layers for creating additional pathways from the distal portions and extremities of the occlusive layer 2002 and paracolic gutters of an abdominal cavity to the fluid removal manifold 2004. In such instances of a multi-layered occlusive layer, such as occlusive layer 2002, the structure may be made from a film material and may be three-dimensionally formed, such as by heat, vacuum, or compression molding.

Still referring to FIG. 17, some embodiments of the treatment device 2001 may include a manifold, such as fluid removal manifold 2004 that is combined with or formed as a part of the occlusive layer 2002. For example, in some embodiments, the fluid removal manifold 2004 may be formed only of a lower manifold film 2016 that is attached or welded to an underside of the occlusive layer 2002, thus obviating the need for an upper manifold film, such as upper manifold film 1014 of FIG. 16. In some additional embodiments, as shown in FIG. 17, the fluid removal manifold 2004 may be positioned with within multiple layers of multi-layered occlusive layer 2002, and thus the lower manifold film 2016 having inlets 2018, may actually be formed as part of a lower layer of the multi-layer occlusive layer 2002. In such embodiments, fluid removal pathways may be present both through perimeter inlets 2026 of the fluid removal manifold 2004 between the various layers of the multi-layered occlusive layer 2002, as well as beneath the fluid removal manifold 2004 and underside of the multi-layered occlusive layer 2002 through inlets 2018. The fluid removal manifold 2004 may include a manifold material 2019 capable of communicating negative pressure and fluid and may include materials such as three-dimensional formed films, wicking materials, and molded manifolds.

In some embodiments, the pressurized distribution vessel 2006 may be combined with or formed as a part of the occlusive layer 2002. For example, in some embodiments, the pressurized distribution vessel 2006 may be formed only of an upper vessel film 2020 that is attached or welded to an upper surface of the occlusive layer 2002, thus eliminating the need for a lower vessel film, such as lower vessel film 1022 of FIG. 16. In some embodiments, the upper vessel film 2020 may be molded with the occlusive layer 2002 as a single structure, as an alternative to being molded and joined from numerous flexible parts. In some instances, the upper vessel film 2020 and occlusive layer 2002 may be quilted to ensure open pathways out of the pressurized distribution vessel 2006. For example, portions of the upper vessel film 2020 and occlusive layer 2002 may be welded together, including a welded perimeter around the portions of the upper vessel film 2020 and the occlusive layer 2002. Additionally, the portions of upper vessel film 2020 and occlusive layer 2002 may be spot welded in a pattern across both of the material layers to create a quilted effect. As a result, in some embodiments, the height and volume of the pressurized distribution vessel 2006 may be restricted when filled with fluid. A variety of materials may be used to form the pressurized distribution vessel 2006, including, but not limited to, small-lumen tubing. In some example embodiments, flow distribution of instillation fluid may be controlled by perimeter outlets 2024, which may be positioned on the perimeter edge(s) of the pressurized distribution vessel 2006. Similar to other embodiments, such perimeter outlets 2024 may be created by techniques such as high-frequency welding. While the illustrative embodiment of FIG. 17 shows modified versions of the occlusive layer 2002, fluid removal manifold 2004, and the pressurized distribution vessel 2006, any combination of these features may be incorporated into a single embodiment.

Figure 18A:
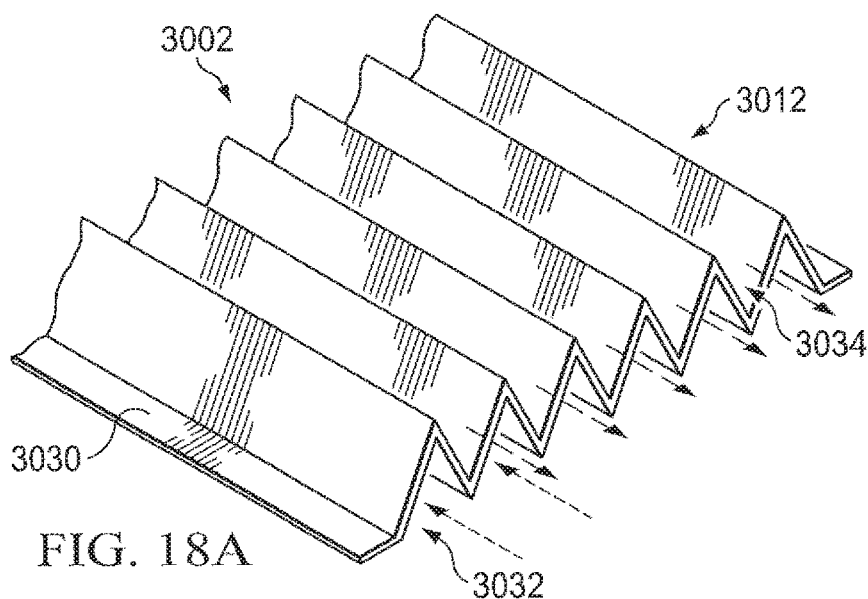
FIGS. 18A-18C are schematic, plan views of illustrative embodiments of portions of the abdominal treatment device of FIG. 15.
Figure 18B:
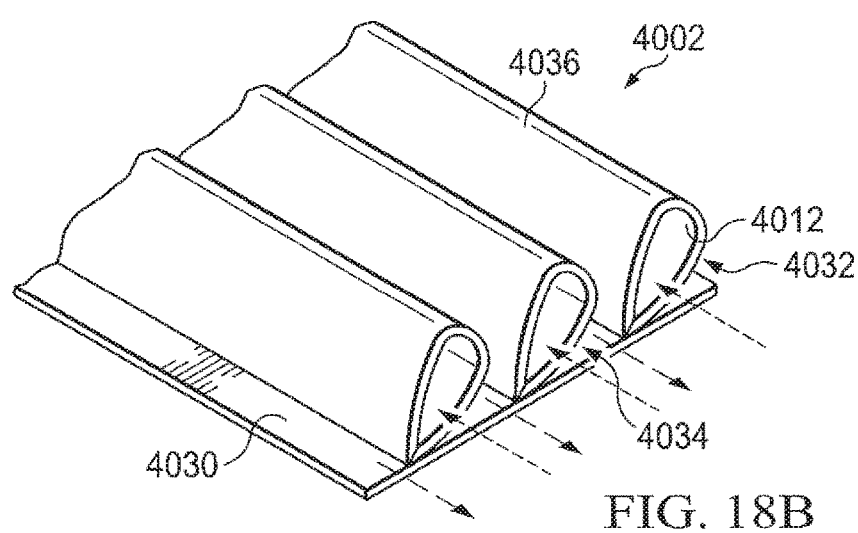
Figure 18C:
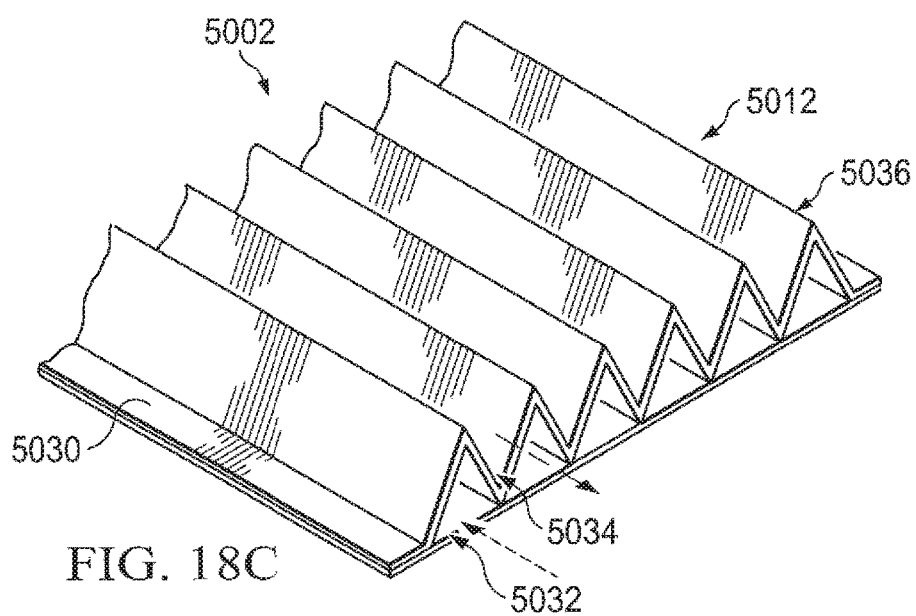

FIGS. 18A-18C illustrate further details associated with features according to some illustrative embodiments of an occlusive layer, such as occlusive layer 1002 of FIG. 15. For example, as shown in FIG. 18A, the occlusive layer 3002 may be formed from a single base layer 3030, which is formed to have a plurality of accordion pleats 3012, which may be equivalent to the pleats 1012 of the occlusive layer 1002 of FIG. 15. The accordion pleats 3012 may form both fluid removal pathways 3032, which may be contained under the lower surface of the base layer 3030, as well as delivery pathways 3034, which may extend along the upper surface of the base layer 3030 forming the accordion pleats 3012.

FIG. 18B shows another illustrative embodiment of an occlusive layer 4002, where instead of fluid pathways formed from accordion pleats 3012, as shown in FIG. 18A, the fluid pathways are formed by tubular pleats 4012. In such embodiments, the occlusive layer 4002 may be formed from a base layer 4030 with a plurality of tubular pleats 4012 formed on an upper surface of the base layer 4030 by separate tubule layers 4036. Alternatively, the tubular pleats 4012 may be formed from the single base layer 4030 that is formed with integral tube-shaped structures, such as by joining or pinching together portions of the base layer 4030 to form the tubular pleats 4012. In any case, the fluid removal pathways 4032 may be provided on the interior of the tubular pleats 4012, and the fluid delivery pathways 4034 may span along the upper surface of the base layer 4030 between the tubular pleats 4012 containing the fluid removal pathways 4032.

FIG. 18C shows another illustrative embodiment of an occlusive layer 5002, similar to that of occlusive layer 4002, however including accordion pleats 5012 for the fluid pathways. Thus, in some embodiments, the occlusive layer 5002 may be formed from a base layer 5030 with a plurality of accordion pleats 5012 formed on an upper surface of the base layer 5030 by separate pleat layer 5036. The removal pathways 5032 may be contained below the pleat layer 5036, or within the space(s) created between the base layer 5030 and the pleat layer 5036. The fluid delivery pathways 5034 may extend along the upper surface of the pleat layer 5036.

Figure 19A:
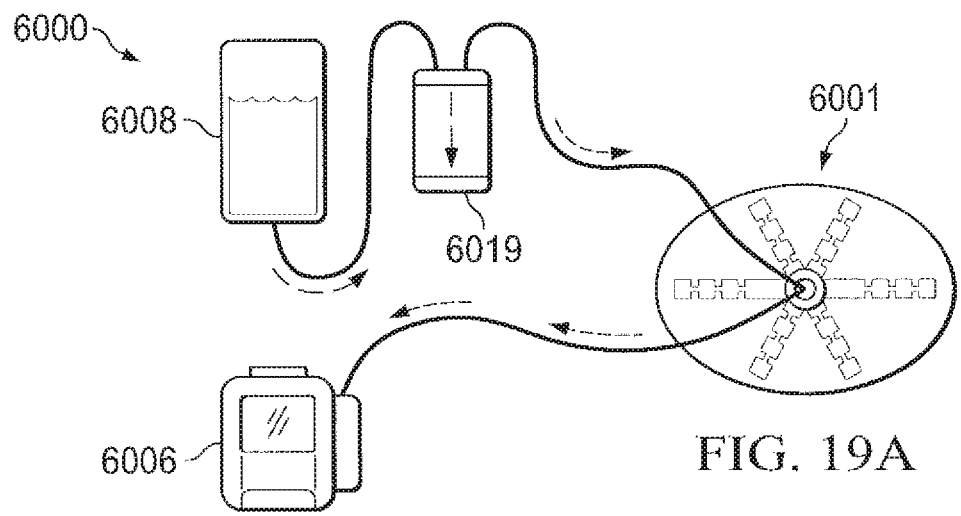
FIGS. 19A-19C are schematic diagrams illustrating the functionality of portions of a therapy system in accordance with this specification, according to some example embodiments.
Figure 19B:
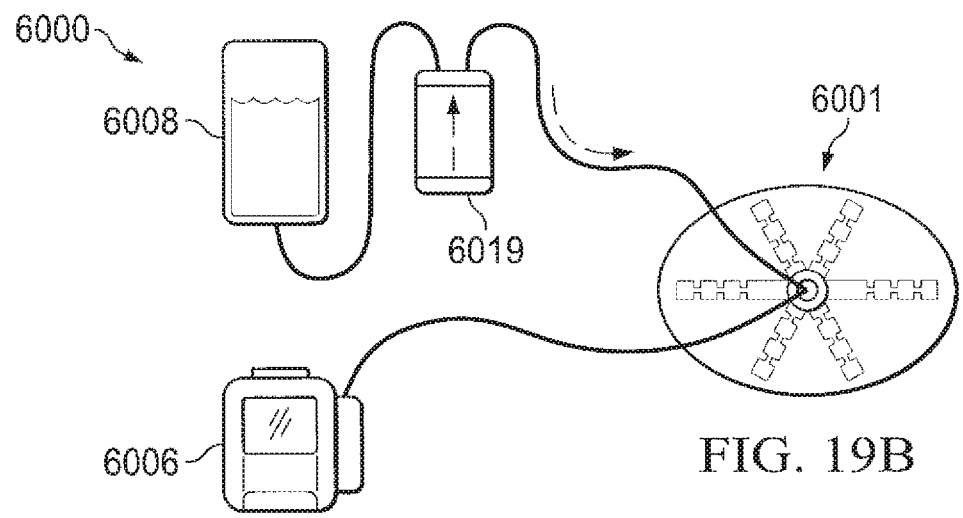
Figure 19C:
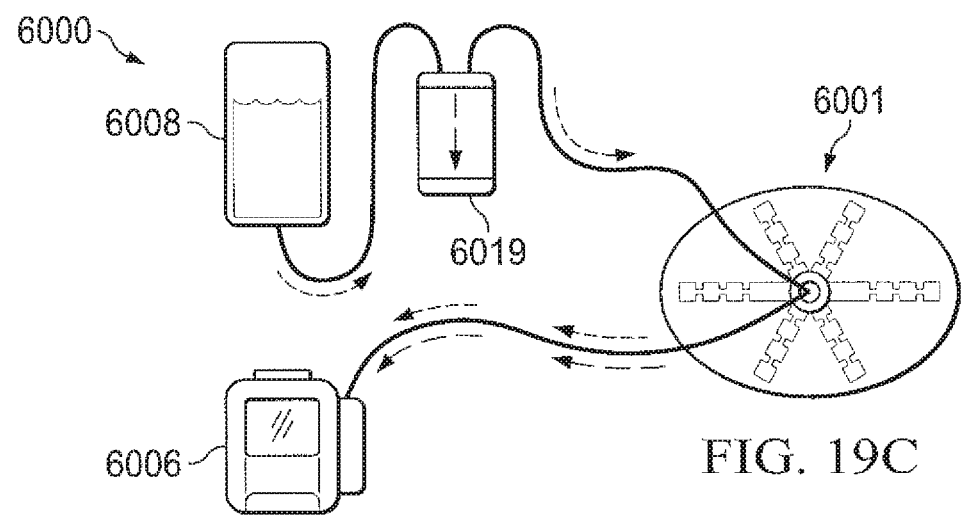

Referring now primarily to FIGS. 19A-19C, further described are additional embodiments of methods for providing negative-pressure therapy and fluid instillation treatment at a tissue site. For example, in some embodiments, a therapy system 6000 may include a treatment device 6001, a negative-pressure source 6006, and a fluid source 6008 that is a separate, standalone device from the negative-pressure source 6006. The fluid source 6008 may be a separate mechanical instillation device. In some embodiments which include a separate mechanical instillation device for the fluid source 6008, the therapy system 6000 may also include an instillation regulator 6019 for monitoring and/or controlling the amount of instillation fluid delivered to the treatment device 6001, and ultimately the tissue site 112. As shown in FIGS. 19A-19C, some disclosed methods may include a therapy cycle including three stages or intervals. For example, as shown in FIG. 19A, a first stage of the therapy cycle may include activating the negative-pressure source 6006 to apply negative-pressure therapy to the treatment device 6001 and tissue site 112. The negative pressure applied by the negative-pressure source 6006 may be communicated through the fluidly connected passageways of the therapy system 6000, and ultimately reach the instillation regulator 6019 and the fluid source 6008. This communicated negative pressure may thus prime the fluid source 6008, which may be a mechanical instillation device. Continuing with FIG. 19B, the method may further include a second stage of the therapy cycle, which may include pausing or ceasing negative-pressure delivery from the negative-pressure source 6006 for a pre-determined interval of time. During this interval, the fluid source 6008, such as a mechanical instillation device, may pass instillation fluid to the instillation regulator 6019, and ultimately to the treatment device 6001. As depicted in FIG. 19C, following a specified interval of delivering instillation fluid from the fluid source 6008 to the treatment device 6001, a third stage of the therapy cycle may be commenced. During this third stage, fluid instillation may be paused, and the negative-pressure source 6006 may be re-activated to provide a further interval of negative-pressure therapy. At this point of the therapy cycle, the instillation fluid may be removed from the treatment device 6001, as well as tissue site 112, such as an abdominal cavity 111. Additionally, the fluid source 6008 may be once again primed and ready to once again deliver instillation fluid to the treatment device 6001, as the second stage of the therapy cycle may be repeated.

Figure 20A:
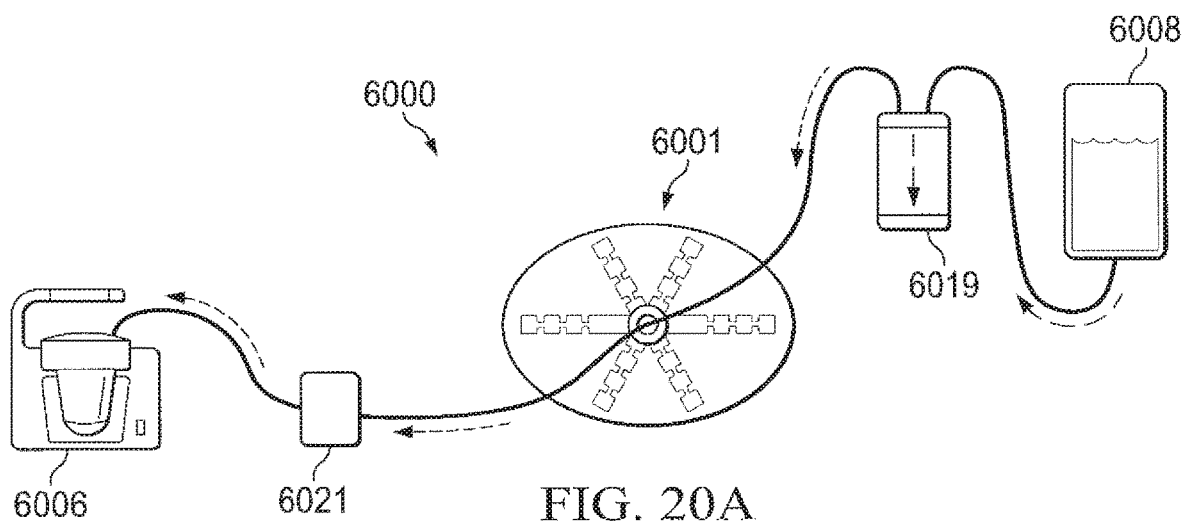
FIGS. 20A-20C are schematic diagrams illustrating the functionality of portions of a therapy system in accordance with this specification, according to some additional example embodiments.
Figure 20B:
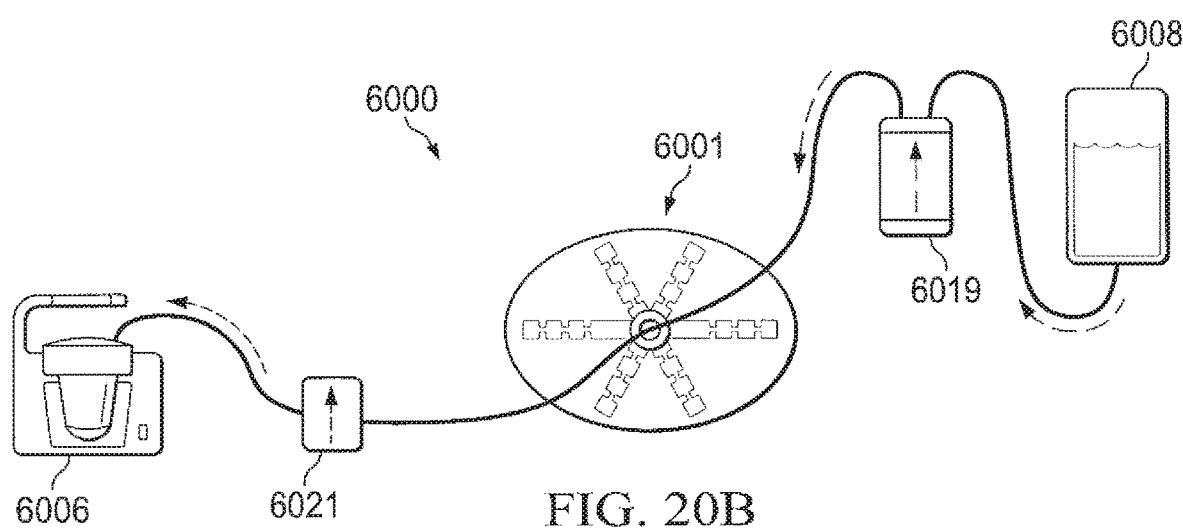
Figure 20C:
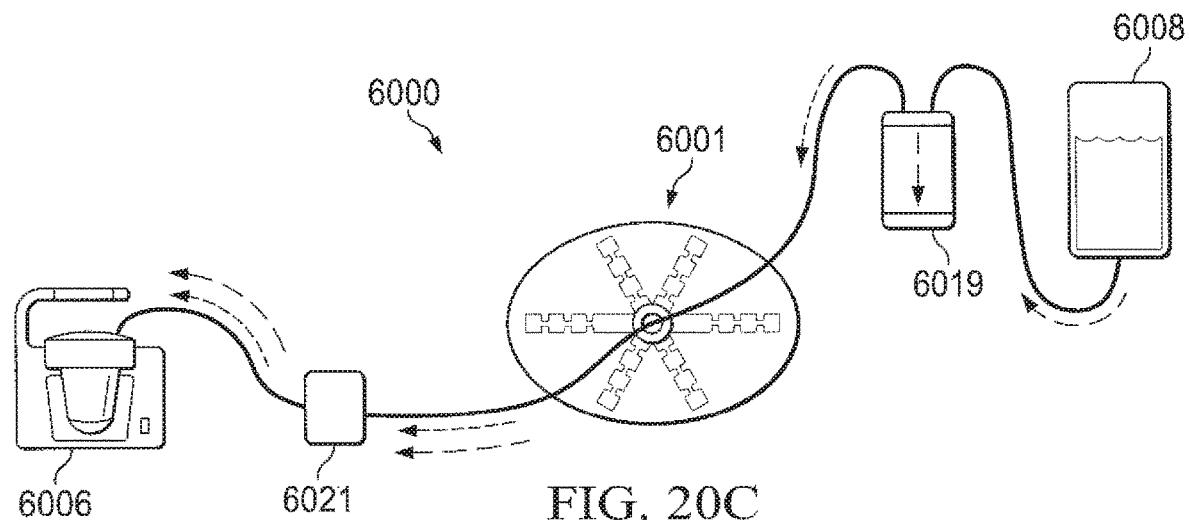

FIGS. 20A-20C illustrate another example embodiment of a method for providing negative-pressure therapy and fluid instillation treatment to a tissue site. The method(s) illustrated by FIGS. 20A-20C may be substantially similar to that described with respect to FIGS. 19A-19C with various modifications. For example, as depicted in FIG. 20A, the therapy system 6000 may include a treatment device 6001, a negative-pressure source 6006, a fluid source 6008, and an instillation regulator 6019. Additionally, the therapy system 6000 may further include a pressure release unit 6021. In some embodiments, during a first stage of a therapy cycle, the negative-pressure source 6006 may be activated to apply negative-pressure therapy to the treatment device 6001. The negative pressure applied by the negative-pressure source 6006 may be communicated through the fluidly connected passageways of the therapy system 6000 and ultimately reach the instillation regulator 6019 and the fluid source 6008. This communicated negative pressure may prime the fluid source 6008, which may be a mechanical instillation device. Continuing with FIG. 20B, the method may further include a second stage of the therapy cycle, during which the pressure release unit 6021 opens and negative-pressure delivery to the treatment device 6001 is stopped. In some embodiments, the pressure release unit 6021 may be opened according to a specific or pre-determined timing schedule. During the second stage of the therapy cycle, the fluid source 6008 may deliver instillation fluid to the instillation regulator 6019, and ultimately to the treatment device 6001, which may occur while the pressure release unit 6021 is opened, thus preventing negative pressure from being communicated to the treatment device 6001 and the fluid source 6008 and instillation regulator 6019. As depicted in FIG. 20C, following the second stage of the therapy cycle, a third stage of the therapy cycle may be begin, during which the pressure release unit 6021 may close, once again according to a timed interval schedule. During the third stage of the therapy cycle, fluid instillation may be paused, and the negative-pressure source 6006 may be re-activated to provide a further interval of negative-pressure therapy. The instillation fluid may be removed from the treatment device 6001, and the fluid source 6008 may be primed and ready to once again deliver instillation fluid to the treatment device 6001.

In some additional methods for providing negative-pressure therapy and fluid instillation to a tissue site, rather than an automated or other form of mechanical instillation device, a manually-controlled instillation vessel, such as a fluid bag, bottle, or other vessel, may be incorporated. Thus, in some embodiments, during a first stage of a therapy cycle, a negative-pressure source may apply negative-pressure therapy to a treatment device and tissue site, while a device such as a clamp, valve, or other form of closure device may prevent fluid from being communicated from the manually-controlled instillation vessel to the treatment device and tissue site. In some embodiments, during a subsequent stage of a therapy cycle, a user may open the clamp or other form of closure device and may manually regulate the volume of fluid being instilled. During this instillation phase, the negative-pressure source may remain active, thus providing immediate removal of the instilled fluid from the treatment device and tissue site. Thus, there may be virtually no dwell time of the fluid in the tissue site, according to some embodiments of the method. The user may then re-clamp or otherwise close the closure device, thus stopping the flow of instillation fluid from the manually-controlled instillation vessel. The negative-pressure source may then continue to remove excess or remaining instillation fluid, as well as exudates, from the treatment device and tissue site. In some other embodiments of the disclosed method, rather than allowing the negative-pressure source to remain active while the fluid is instilled from the manually-controlled instillation vessel, the negative-pressure source may be paused, thus allowing the instillation fluid to dwell in the tissue site for a prescribed period of time. When appropriate, the user may close off the manually-controlled instillation vessel from delivering instillation fluid. Prior or subsequent to instillation being stopped, negative-pressure therapy may be recommenced, during which time any excess or remaining fluids may be removed from the treatment device and tissue site.

The systems, apparatuses, and methods described herein may provide significant advantages. As previously discussed, the disclosed systems and devices may provide a combined temporary abdominal closure dressing system with fluid instillation capability through an independent matrix of fluid delivery tubing, as well as negative-pressure fluid removal pathways for removal of contaminated fluid. Thus, the disclosed embodiments may provide means for irrigating and cleansing an abdominal cavity while supporting and protecting the abdominal contents, as well as removing contaminated fluid and controlling and/or reducing edema. Additionally, as a result of the various layers and components of the disclosed dressings applying tension and closing force to the abdominal contents, quicker primary facial closure of the abdominal cavity may be facilitated.

As described herein, the disclosed solutions may provide means for irrigating all areas of an abdominal cavity, including small bowel loops, gutters, retroperitoneal space, portions of the lymphatic system, etc., all while the dressing system is in place, thus reducing time required for patients and clinical staff in the operating room. The various embodiments described offer various configurations of fluid pathways designed to maximize the exposure of internal organs of abdominal tissue sites to fluid instillation therapy. The disclosed dressing components may also allow for longer dressing application times without adhering to the fascia of abdominal tissue sites. Thus, repeatable as well as reliable fluid instillation that may be provided evenly to various portions of a tissue site may be provided. As a result, fluid irrigation and cleansing may be more consistent, thus leading to a reduction in mortality of patients suffering from septic abdominal cavities. Fluid instillation may be managed at a patient's bedside and may be custom-tailored and adjusted on a case-by-case basis.

The disclosed systems and devices may drain exudate and infectious material from tissue sites, such as the abdominal cavity, therefore reducing the presence of contaminated abdominal fluids to promote healing. Furthermore, the disclosed solutions may provide separate instillation and negative-pressure pathways to ensure that contaminated, or "dirty," fluid is fully removed from the abdomen. Furthermore, in preferred embodiments of the disclosed systems, instillation fluid is not recirculated back into the tissue site. As a result, the clinical benefits of irrigating tissue sites may be increased.

Importantly, the design of the disclosed devices may also allow for user sizing and/or customization at the time of application to a patient in the operating room. In some embodiments, improved ease of use for dressing placement, sizing, and removal may be provided by built-in sizing or placement visual markings or indicators for guiding users. Some embodiments of the disclosed dressing systems may also include various components, such as the fluid instillation pathways and/or fluid removal pathways already pre-attached to the structural dressing layers to further streamline and simplify use. As a result, not only may improved fluid delivery as well as removal be enabled as compared to existing dressing systems, but increased ease of use may be promoted.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context. Further, any feature described in connection with any one embodiment may also be applicable to any other embodiment. Components may be also be combined or eliminated in various configurations for purposes of sale, manufacture, assembly, or use. For example, in some configurations the treatment device 101 including the dressing 102, the container 110, or both may be eliminated or separated from other components for manufacture or sale.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A dressing for treating a tissue site, comprising:
a dressing member comprising a first protective layer and a second protective layer, the first protective layer coupled to the second protective layer by a first plurality of linear welds and a second plurality of linear welds, wherein:
each linear weld of the first plurality of linear welds extends a distance from an area proximate a center of the dressing member towards an outer edge of the dressing member, the first plurality of linear welds defining a plurality of fluid removal pathways between the first protective layer and the second protective layer,
each linear weld of the second plurality of welds extends a distance from the area proximate the center of the dressing member towards the outer edge of the dressing member, the second plurality of linear welds defining a plurality of instillation pathways between the first protective layer and the second protective layer, and
wherein a pair of the first plurality of linear welds defining each of the fluid removal pathways is positioned in an alternating arrangement with a pair of the second plurality of linear welds defining each of the instillation pathways;
a plurality of manifold members encapsulated between the first protective layer and the second protective layer, each manifold member extending substantially along a length of each fluid removal pathway from the area proximate the center of the dressing member towards the outer edge of the dressing member; and
an instillation matrix comprising a plurality of fluid delivery tubes encapsulated between the first protective layer and the second protective layer, each fluid delivery tube extending substantially along a length of each instillation pathway from the area proximate the center of the dressing member towards the outer edge of the dressing member.

2. The dressing of claim 1, wherein the manifold members comprise an open-cell reticulated polyurethane foam.

3. The dressing of claim 2, wherein the open-cell reticulated polyurethane foam has a thickness of between 5 mm and 15 mm.

4. The dressing of claim 1, further comprising a hub positioned proximate to the center of the dressing member and in fluid communication with the instillation matrix.

5. The dressing of claim 4, wherein the hub comprises medical grade silicone.

6. The dressing of claim 4, wherein the hub comprises medical grade PVC.

7. The dressing of claim 4, wherein:
the hub comprises a plurality of openings sized and configured to control fluid flow into the plurality of fluid delivery tubes.

8. The dressing of claim 7, wherein the plurality of fluid delivery tubes are connected to the plurality of openings of the hub with a medical grade adhesive.

9. The dressing of claim 7, wherein the plurality of fluid delivery tubes are connected to the plurality of openings of the hub with cyclohexanol.

10. The dressing of claim 1, wherein a size of the dressing may be reduced by removing a portion of an outer perimeter of the dressing.

11. The dressing of claim 1, wherein the plurality of fluid delivery tubes comprises silicone.

12. The dressing of claim 1, wherein the instillation matrix comprises PVC tubing.

13. The dressing of claim 1, wherein the instillation matrix comprises tubing having an interior diameter of about 1 mm to 2 mm.

14. The dressing of claim 1, wherein the first protective layer and the second protective layer are ultrasonically welded together.

15. A dressing for treating a tissue site, comprising:
a first liquid impermeable layer;
a second liquid impermeable layer positioned against and substantially coextensive with the first liquid impermeable layer;
a plurality of linear welds coupling the first liquid impermeable layer to the second liquid impermeable layer, each weld extending a distance from an area proximate a center of the dressing towards a periphery of the dressing;
a plurality of fluid pathways formed between the first liquid impermeable layer, the second liquid impermeable layer, and pairs of the plurality of linear welds;
a perforated joint positioned between each of the plurality of fluid pathways and extending through the periphery of the dressing, wherein each of the plurality of fluid pathways is configured to be individually moveable by separation of the perforated joint;
a manifold member disposed in each fluid pathway, the manifold member extending a length between the area proximate the center of the dressing towards the periphery of the dressing; and
a fluid delivery tube disposed in each fluid pathway, the fluid delivery tube disposed external to and adjacent to an exterior surface of the manifold member and extending the length between the area proximate the center of the dressing towards the periphery of the dressing, the fluid delivery tube comprising at least one perforation for delivering a fluid, the at least one perforation in direct fluid communication with an interior of the fluid pathway between the first liquid impermeable layer, the second liquid impermeable layer, and one of the pairs of linear welds.

16. The dressing of claim 15, wherein the plurality of linear welds are ultrasonic welds.

17. The dressing of claim 16, wherein the first liquid impermeable layer further comprises perforations along the plurality of fluid pathways.

18. The dressing of claim 15, wherein the first liquid impermeable layer and the second liquid impermeable layer each comprises a polyurethane film.

19. The dressing of claim 18, wherein the first liquid impermeable layer and the second liquid impermeable layer each has a thickness of between 25 micrometers and 500 micrometers.

20. The dressing of claim 15, wherein the fluid delivery tube is positioned alongside the manifold member and extends substantially parallel with the manifold member.

21. The dressing of claim 15, wherein the first liquid impermeable layer and the second liquid impermeable layer comprise perforations.

22. The dressing of claim 15, further comprising a fluid hub fluidly connected to the fluid delivery tube and configured to control distribution of fluid to the fluid delivery tube.

23. The dressing of claim 15, wherein the fluid delivery tube comprises perforations along its length.

24. The dressing of claim 15, wherein the fluid delivery tube comprises an opening at an end furthest from the center of the dressing.

25. The dressing of claim 15, wherein the plurality of fluid pathways are spaced by an approximately equal angle of separation.

26. The dressing of claim 15, wherein the fluid delivery tube comprises a lower profile tube.

27. The dressing of claim 15, wherein the fluid delivery tube comprises perforations along its length and has a closed end that is furthest from the center of the dressing.

28. The dressing of claim 15, further comprising a fluid hub fluidly connected to the fluid delivery tube.

\* \* \* \* \*